United States Patent
Roughley et al.

(10) Patent No.: US 10,383,871 B2
(45) Date of Patent: *Aug. 20, 2019

(54) AZETIDINE DERIVATIVES

(71) Applicant: Vernalis (R&D) Ltd, Winnersh, Berkshire (GB)

(72) Inventors: Stephen Roughley, Great Abington, Cambridge (GB); Steven Walls, Great Abington, Cambridge (GB); Terance Hart, Great Abington, Cambridge (GB); Rachel Parsons, Great Abington, Cambridge (GB); Paul Brough, Great Abington, Cambridge (GB); Christopher Graham, Great Abington, Cambridge (GB); Alba Macias, Great Abington, Cambridge (GB)

(73) Assignee: Vernalis (R&D) Ltd., Great Abington, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/278,386

(22) Filed: Sep. 28, 2016

(65) Prior Publication Data

US 2017/0196864 A1    Jul. 13, 2017

Related U.S. Application Data

(60) Continuation of application No. 14/641,783, filed on Mar. 9, 2015, now Pat. No. 9,475,800, which is a continuation of application No. 13/866,059, filed on Apr. 19, 2013, now Pat. No. 9,006,269, which is a division of application No. 12/920,181, filed as application No. PCT/GB2009/000568 on Feb. 27, 2009, now Pat. No. 8,450,346.

(30) Foreign Application Priority Data

Apr. 5, 2008 (GB) .................................. 0804006.5
Nov. 27, 2008 (GB) .................................. 0821694.7

(51) Int. Cl.
| A61K 31/397 | (2006.01) |
| A61K 31/497 | (2006.01) |
| A61K 31/495 | (2006.01) |
| A61K 31/506 | (2006.01) |
| A61K 31/4427 | (2006.01) |
| C07D 205/04 | (2006.01) |
| C07D 401/12 | (2006.01) |
| C07D 401/14 | (2006.01) |
| C07D 413/14 | (2006.01) |
| A61K 31/4439 | (2006.01) |
| A61K 31/501 | (2006.01) |

(52) U.S. Cl.
CPC .......... *A61K 31/506* (2013.01); *A61K 31/397* (2013.01); *A61K 31/4427* (2013.01); *A61K 31/4439* (2013.01); *A61K 31/495* (2013.01); *A61K 31/497* (2013.01); *A61K 31/501* (2013.01); *C07D 205/04* (2013.01); *C07D 401/12* (2013.01); *C07D 401/14* (2013.01); *C07D 413/14* (2013.01)

(58) Field of Classification Search
CPC ............ A61K 31/4427; A61K 431/397; A61K 31/495; A61K 31/397
USPC ............................ 514/210.17, 247, 332, 336
See application file for complete search history.

(56) References Cited

U.S. PATENT DOCUMENTS

| 5,183,902 A | * 2/1993 | Taylor, Jr. ............ A61K 31/395 548/950 |
| 6,335,445 B1 | 1/2002 | Chabrier de Lassauniere et al. |
| 9,475,800 B2 | * 10/2016 | Roughley ............ C07D 205/04 |

FOREIGN PATENT DOCUMENTS

| WO | 99/37614 A1 | 7/1999 |
| WO | 9937614 A1 | 7/1999 |
| WO | 2005090347 A1 | 9/2005 |

OTHER PUBLICATIONS

Ahn et al, Fatty acid amide hydrolase as a potential therapeutic target for the treatment of pain and CNS disorders, Exper Opin. Drug Discov (2009), vol. 4(7), pp. 763-784.*

(Continued)

*Primary Examiner* — Craig D Ricci
*Assistant Examiner* — Janet L. Coppins
(74) *Attorney, Agent, or Firm* — Banner & Witcoff, Ltd.

(57) ABSTRACT

Compounds of formula (I) are inhibitors of fatty acid amide hydrolase, (FAAH), and which are useful in the treatment of diseases or medical conditions which benefit from inhibition of FAAH activity, such as anxiety, depression pain, inflammation, and eating, sleep, neurodegenerative and movement disorders:

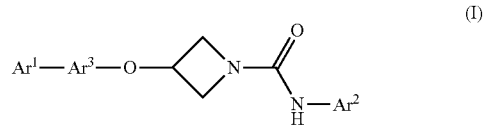

(I)

$Ar^1$ is optionally substituted phenyl or optionally substituted monocyclic heteroaryl having 5 or 6 ring atoms; $Ar^2$ is optionally substituted phenyl, optionally substituted monocyclic heteroaryl having 5 or 6 ring atoms or optionally substituted fused bicyclic heteroaryl having 5 or 6 ring atoms in each fused ring; and $Ar^3$ is a divalent radical selected from optionally substituted phenylene and optionally substituted monocyclic heteroarylene radicals having 5 or 6 ring atoms.

13 Claims, No Drawings

(56) References Cited

OTHER PUBLICATIONS

Ahn et al, Fatty acid amide hydrolase as a potential therapeutic target for the treatment of pain and CNS disorders, Exper Opin. Drug Discov (2009), vol. 4(7), pp. 763-784. (Year: 2009).*
Pacher et al, Pharmacological Reviews, 2006, vol. 58, pp. 389-462. (Year: 2006).*
Schneider et al, Neuroscience and Biobehavioral Reviews (2017), vol. 76, pp. 336-362. (Year: 2017).*
International Search Report for PCT/GB2009/000568 dated May 29, 2009.
Nakamura, et al. Transition-Metal-Catalyzed Reactions in Heterocyclic Synthesis, Chem. Rev. 2004, vol. 104, p. 2127.
Banfi, L. Et al. Ugi Multicomponent Reaction Followed by an Intermolecular Nucleophilic Substitution; Convergen Multicomponene Synthesis of 1-sulfonyl 1,4-diazepan-5-ones and of their benzofuzed Derivatives. J. Org. Chem. 2007, vol. 72, p. 2151.
Dorwold, FZ, Side Reactions in Organic Synthesis. Wiley, 2005, preface.
Cravatt, B.G., et al., Fatty acid amide hydrolase; an emerging therapeutic target in the endocannabinoid system. Current Opinion in chemical biology, 2003, vol. 7, p. 473.

\* cited by examiner

AZETIDINE DERIVATIVES

CROSS REFERENCE TO RELATED APPLICATIONS

This application is a continuation of U.S. application Ser. No. 14/641,783, filed Mar. 9, 2015, now pending, which is a continuation of U.S. application Ser. No. 13/866,059, filed Apr. 19, 2013, now U.S. Pat. No. 9,006,269, issued Apr. 14, 2015, which is a division of U.S. application Ser. No. 12/920,181, filed Apr. 20, 2011, now U.S. Pat. No. 8,450,446, issued May 28, 2013, which is a U.S. National Stage application of co-pending PCT application PCT/GB2009/000568 filed Feb. 27, 2009, which claims the benefit of Great Britain application number 0804006.5 filed Mar. 4, 2008 and Great Britain application number 0821694.7 filed Nov. 27, 2008. These applications are incorporated herein by reference in their entireties.

This invention relates to a class of azetidine derivatives which are inhibitors of fatty acid amide hydrolase, (FAAH), and which are useful in the treatment of diseases or medical conditions which benefit from inhibition of FAAH activity, such as anxiety, depression pain, inflammation, and eating, sleep, neurodegenerative and movement disorders.

BACKGROUND TO THE INVENTION

The endogenous agonists of the cannabinoid receptors CB1 and CB2 include the fatty acid amide anandamide (AEA). AEA is hydrolysed to arachidonic acid by the membrane bound protein fatty acid amide hydrolase (FAAH). FAAH was characterized in 1996 by Cravatt and co-workers (Cravatt, Nature 1996, 384, 83). It was subsequently determined that FAAH is additionally responsible for the catabolism of a large number of important lipid signaling fatty acid amides including: another major endocannabinoid, 2-arachidonoylglycerol (2-AG) (Science 1992, 258, 1946-1949); the sleep-inducing substance, oleamide (Science 1995, 268, 1506); the appetite-suppressing agent, N-oleoylethanolamine (OEA) (Rodriguez de Fonesca, Nature 2001, 414, 209); and the anti-inflammatory agent, palmitoylethanolamide (PEA) (Lambert, Curr. Med. Chem. 2002, 9(6), 663).

Inhibitors of FAAH are being sought since such inhibitors elevate the concentrations of these endogenous signaling lipids and thereby produce associated beneficial pharmacological effects. There have been some reports of the effects of various FAAH inhibitors in pre-clinical models. Those effects include analgesic properties (see WO 02/087569, WO 04/033652); anxiety (Kathuria, Nat. Med. 2003, 9(1), 76); spasticity (Baker, FASEB J. 2001, 15(2), 300).

Results of research on the effects of certain exogenous cannabinoids also suggest that a FAAH inhibitor may be useful for treating various conditions, diseases, disorders, or symptoms. These include pain, nausea/emesis, anorexia, spasticity, movement disorders, epilepsy and glaucoma. To date, approved therapeutic uses for cannabinoids include the relief of chemotherapy-induced nausea and emesis among patients with cancer and appetite enhancement in patients with HIV/AIDS who experience anorexia as a result of wasting syndrome.

Apart from the approved indications, a therapeutic field that has received much attention for cannabinoid use is analgesia, i.e., the treatment of pain. Five small randomized controlled trials showed that tetrahydrocannabinol THC is superior to placebo, producing dose-related analgesia (Robson, Br. J. Psychiatry 2001, 178, 107-115).

A number of individuals with multiple sclerosis have claimed a benefit from *cannabis* for both disease-related pain and spasticity, with support from small controlled trials (Svendsen, Br. Med. J. 2004, 329, 253). Likewise, various victims of spinal cord injuries, such as paraplegia, have reported that their painful spasms are alleviated after smoking marijuana. A report showing that cannabinoids appear to control spasticity and tremor in the CREAE model of multiple sclerosis demonstrated that these effects are mediated by CB1 and CB2 receptors (Baker, Nature 2000, 404, 84-87). Phase 3 clinical trials have been undertaken in multiple sclerosis and spinal cord injury patients with a narrow ratio mixture of tetrahydrocannabinol/cannabidiol (THC/CBD).

Cannabinoids produced dose-related reductions in intraocular pressure (IOP) and therefore may relieve glaucoma symptoms. Ophthalmologists have prescribed *cannabis* for patients with glaucoma in whom other drugs have failed to adequately control intraocular pressure (Robson, 2001 supra).

In addition to the effects of a FAAH inhibitor on AEA and other endocannabinoids, inhibitors of FAAH's catabolism of other lipid mediators may be used in treating other therapeutic indications. For example, PEA has demonstrated biological effects in animal models of inflammation, immunosuppression, analgesia, and neuroprotection (Ueda, J. Biol. Chem. 2001, 276(38), 35552). Oleamide, another substrate of FAAH, induces sleep (Boger, Proc. Natl. Acad. Sci. USA 2000, 97(10), 5044; Mendelson, Neuropsychopharmacology 2001, 25, S36).

FAAH inhibitors are considered potentially useful in treating Alzheimer's Disease, schizophrenia, depression, alcoholism, addiction, suicide, Parkinson's disease, Huntington's disease, stroke, emesis, miscarriage, embryo implantation, endotoxic shock, liver cirrhosis, atherosclerosis, cancer, traumatic head injury, glaucoma, and bone cement implantation syndrome.

Other diseases or medical conditions that would potentially benefit from inhibition of FAAH activity, include, for example, multiple sclerosis, retinitis, amyotrophic lateral sclerosis, immunodeficiency virus-induced encephalitis, attention-deficit hyperactivity disorder, pain, nociceptive pain, neuropathic pain, inflammatory pain, non-inflammatory pain, painful hemorrhagic cystitis, obesity, hyperlipidemia, metabolic disorders, feeding and fasting, alteration of appetite, stress, memory, aging, hypertension, septic shock, cardiogenic shock, intestinal inflammation and motility, irritable bowel syndrome, colitis, diarrhea, ileitis, ischemia, cerebral ischemia, hepatic ischemia, myocardial infarction, cerebral excitotoxicity, seizures, febrile seizures, neurotoxicity, neuropathies, sleep, induction of sleep, prolongation of sleep, insomnia, and inflammatory diseases.

Neurological and psychological diseases or conditions that would potentially benefit from inhibition of FAAH activity include, for example, pain, depression, anxiety, glaucoma, nausea, emesis, loss of appetite, sleep disturbances, respiratory disorders, allergies, traumatic brain injury, stroke, generalized anxiety disorder (GAD), obsessive compulsive disorders, stress, stress urinary incontinence, attention deficit hyperactivity disorders, schizophrenia, psychosis, Parkinson's disease, muscle spasticity, epilepsy, dyskenesia, seizure disorders, jet lag, and insomnia.

Other diseases or medical conditions that would potentially benefit from inhibition of FAAH activity, include, for example, a variety of metabolic syndromes, diseases, disorders and/or conditions, including but not limited to, insulin resistance syndrome, diabetes, hyperlipidemia, fatty liver disease, obesity, atherosclerosis and arteriosclerosis.

FAAH inhibitors are potentially useful in the treatment of a variety of painful syndromes, diseases, disorders and/or conditions, including but not limited to those characterized by non-inflammatory pain, inflammatory pain, peripheral neuropathic pain, central pain, deafferentiation pain, chronic nociceptive pain, stimulus of nociceptive receptors, phantom and transient acute pain.

Inhibition of FAAH activity can also potentially be used in the treatment of a variety of conditions involving inflammation. These conditions include, but are not limited to arthritis (such as rheumatoid arthritis, shoulder tendonitis or bursitis, gouty arthritis, and aolymyalgia rheumatica), organ-specific inflammatory diseases (such as thyroiditis, hepatitis, inflammatory bowel diseases), asthma, other autoimmune diseases (such as multiple sclerosis), chronic obstructive pulmonary disease (COPD), allergic rhinitis, and cardiovascular diseases.

FAAH inhibitors are potentially useful in preventing neurodegeneration or for neuroprotection.

In addition, it has been shown that when FAAH activity is reduced or absent, one of its substrates, anandamide, acts as a substrate for COX-2, which converts anandamide to prostamides (Weber et al. J. Lipid. Res. 2004; 45:757). Concentrations of certain prostamides may be elevated in the presence of a FAAH inhibitor. Certain prostamides are associated with reduced intraocular pressure and ocular hypotensivity. Thus, FAAH inhibitors may be useful for treating glaucoma.

BRIEF SUMMARY OF THE INVENTION

This invention makes available a class of azetidine derivatives, more fully defined and described below, having FAAH inhibitory activity. The compounds of the invention are useful for treatment of diseases or medical conditions which benefits from inhibition of FAAH activity. Such diseases or conditions have been described above. In particular the compounds of the invention may be used in the treatment of anxiety, depression, pain, inflammation, a sleep disorder or a movement disorder.

DETAILED DESCRIPTION OF THE INVENTION

In one aspect, the present invention provides a compound of formula (I), or a pharmaceutically acceptable salt thereof:

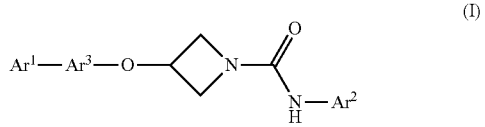

(I)

wherein
$Ar^1$ is optionally substituted phenyl or optionally substituted monocyclic heteroaryl having 5 or 6 ring atoms;
$Ar^2$ is optionally substituted phenyl, optionally substituted monocyclic heteroaryl having 5 or 6 ring atoms or optionally substituted fused bicyclic heteroaryl having 5 or 6 ring atoms in each fused ring; and
$Ar^3$ is a divalent radical selected from the group consisting of optionally substituted phenylene and optionally substituted monocyclic heteroarylene radicals having 5 or 6 ring atoms.

In other aspects, the invention provides
(a) a pharmaceutical composition comprising a compound of formula (I) above or a pharmaceutically acceptable salt thereof, together with one or more pharmaceutically acceptable carriers and/or excipients;
(b) The use of compound of formula (I) above or a pharmaceutically acceptable salt thereof, for treatment of a disease or medical condition which benefits from inhibition of FAAH activity;
(c) a method of treatment of a disease or medical condition which benefits from inhibition of FAAH activity, comprising administering to a subject suffering such disease or condition an effective amount of compound of formula (I) above or a pharmaceutically acceptable salt thereof.

Diseases or medical conditions which benefit from inhibition of FAAH activity include those referred to above, and in particular include anxiety, depression, pain (especially nociceptive, neuropathic, visceral, post operative pain and pain caused by cancer), pruripus, inflammation, sleep disorders and movement disorders.

Terminology

As used herein, the term "$(C_a$-$C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein, the term "$(C_a$-$C_b)$fluoroalkyl" wherein a and b are integers refers to a straight or branched chain alkyl radical having from a to b carbon atoms in which one or more hydrogen atoms are replaced by fluorine atoms. Mono- di- and tri-fluoromethyl are encompassed by this term.

As used herein the unqualified term "heteroaryl" refers to a monocyclic or fused bicyclic aromatic radical containing one or more heteroatoms selected from S, N and O. A monocyclic heteroaryl radical may in particular have 5 or 6 ring atoms. In a fused bicyclic heteroaryl radical each fused ring may have 5 or 6 ring atoms. Illustrative of heteroaryl radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

A "divalent phenylene radical" is a benzene ring with two unsatisfied valencies, and includes 1,3-phenylene and 1,4-phenylene.

A "divalent heteroarylene radical" is a heteroaryl ring in which two ring carbon atoms have unsatisfied valencies. For example monocyclic divalent heteroarylene radicals having six ring atoms include the following pyridinylene, pyrimidinylene, and pyrazinylene radicals:

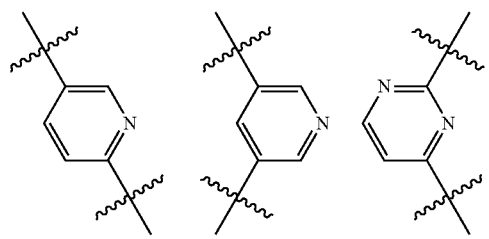

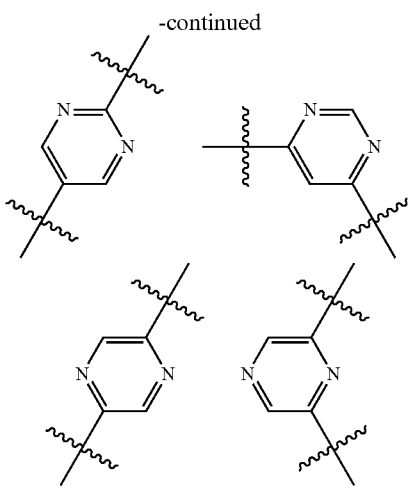

Monocyclic divalent heteroarylene radicals having five ring atoms include those of the following formulae:

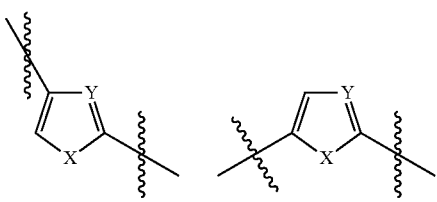

wherein X is —NH—, —N(CH$_3$)—, N(CH$_2$CH$_3$)—. —O— or —S—, and Y is =C— or =NH—.

Unless otherwise specified in the context in which it occurs, the term "substituted" as, applied to any phenyl or heteroaryl moiety herein means substituted with at least one substituent, for example selected from (C$_1$-C$_6$)alkyl, (C$_1$-C$_6$)fluoroalkyl, (C$_1$-C$_6$)alkoxy (including methylenedioxy and ethylenedioxy substitution on adjacent carbon atoms of an aromatic ring), (C$_1$-C$_6$)fluoroalkoxy, (C$_1$-C$_6$)alkoxy-(C$_1$-C$_6$)alkyl, benzyloxy-(C$_1$-C$_6$)alkyl, (C$_1$-C$_6$)alkoxy-(C$_1$-C$_6$)alkoxy, benzyloxy-(C$_1$-C$_6$)alkoxy, hydroxy, hydroxy(C$_1$-C$_6$)alkyl, hydroxy(C$_1$-C$_6$)alkoxy, mercapto, mercapto(C$_1$-C$_6$)alkyl, (C$_1$-C$_6$)alkylthio, cyclopropyl, halo (including fluoro and chloro), nitro, nitrile (cyano), —COOH, tetrazolyl, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$-COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$ or —NR$^A$CONR$^A$R$^B$ wherein R$^A$ and R$^B$ are independently a (C$_1$-C$_4$)alkyl group, or R$^A$ and R$^B$ when attached to the same nitrogen may form, together with that nitrogen, a cyclic amino group such as a morpholinyl, piperidinyl or piperazinyl group. An "optional substituent" may be one of the substituent groups encompassed in the above description.

As used herein the term "salt" includes base addition, acid addition and quaternary salts. Compounds of the invention which are acidic can form salts, including pharmaceutically or veterinarily acceptable salts, with bases such as alkali metal hydroxides, e.g. sodium and potassium hydroxides; alkaline earth metal hydroxides e.g. calcium, barium and magnesium hydroxides; with organic bases e.g. N-ethyl piperidine, dibenzylamine and the like. Those compounds (I) which are basic can form salts, including pharmaceutically or veterinarily acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic and p-toluene sulphonic acids and the like. Any unqualified reference herein to a compound which falls within formula (I) is to be construed as a reference to that compound, irrespective of whether it is or is not in the form of salt.

For a review on suitable salts, see *Handbook of Pharmaceutical Salts: Properties, Selection, and Use* by Stahl and Wermuth (Wiley-VCH, Weinheim, Germany, 2002).

In common with many organic compounds useful in medicine, at least some of the compounds of the invention are expected to be recoverable as crystalline hydrates and solvates. Such hydrates and solvates are of course merely specific physico-chemical forms of the active compounds of the invention and therefore form part of the invention. Any unqualified reference herein to a compound which falls within formula (I) is to be construed as a reference to that compound, irrespective of whether it is or is not in the form of a hydrate or solvate. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Structural Features

In the compounds of the invention:

Ar$^1$ may be optionally substituted phenyl, or may be selected from the group of monocyclic heteroaryl groups consisting of, for example, pyridyl, thienyl, furyl, pyrrolyl, imidazolyl, oxazolyl, isoxazolyl, thiazolyl, isothiazolyl, pyrazolyl, triazolyl, oxadiazolyl, thiadiazolyl, pyridazinyl, pyrimidinyl, pyrazinyl, tetrazolyl, and triazinyl, any of which being optionally substituted. In particular cases, Ar$^1$ is phenyl, 2-, 4- or 5-oxazolyl, 2-, 4- or 5-thiazolyl, [1,3,4]thiadiazol-2-yl, [1,3,4]oxadiazol-2-yl, [1,2,3]oxadiazol-4-yl, 1-, 4-pyrazolyl, or [1,2,4]triazol-3-yl, any of which being optionally substituted. In specific cases, Ar$^1$ may be, for example, phenyl, 2-fluorophenyl, 3-(2-methoxy-ethoxy)-phenyl, or 2-methoxy-5-(2-methoxy-ethoxy)-phenyl.

Ar$^2$ may be optionally substituted phenyl; or may be selected from the group of monocyclic heteroaryl groups consisting of, for example, pyridyl, thienyl, furyl, pyrrolyl, imidazolyl, oxazolyl, isoxazolyl, thiazolyl, isothiazolyl, pyrazolyl, triazolyl, oxadiazolyl, thiadiazolyl, pyridazinyl, pyrimidinyl, pyrazinyl, and triazinyl, any of which being optionally substituted; or may be selected from the group of fused bicyclic heteroaryl groups consisting of, for example, benzthienyl, benzfuryl, benzimidazolyl, benzthiazolyl, benzisothiazolyl, pyrazolyl, benzoxazolyl, benzisoxazolyl, benztriazolyl, indolyl and indazolyl, any of which being optionally substituted. In particular cases, Ar$^2$ is phenyl, 2-, 3- or 4-pyridyl, 2-, 4 or 5-pyrimidinyl, pyrazin-2-yl, pyridazin-3-yl, 2-thiazolyl, 2-oxazolyl, benz[d]isoxazol-3-yl, indazol-3-yl, 5-oxadiazolyl, or 5-thiadiazolyl, any of which being optionally substituted.

Currently preferred Ar$^2$ groups include phenyl, pyridyl, pyrimidinyl, pyrazinyl or pyridazinyl; any of which being optionally substituted. For example, Ar$^2$ may be 3-pyridyl, pyrimidin-4-yl, pyrazin-2-yl or pyridazin-3-yl.

Ar$^3$ may be an optionally substituted phenylene radical, such as; for example, a 1,4-phenylene radical; or may be selected from the group consisting of, for example, divalent pyridinylene, thienylene, furylene, pyrrolylene, imidazolylene, oxazolylene, isoxazolylene, thiazolylene, isothiazolylene, pyrazolylene, triazolylene, pyridazinylene, pyrimidinylene, pyrazinylene, triazinylene, thiadiazolylene radicals, any of which being optionally substituted.

Currently preferred $Ar^3$ radicals include phenylene or pyridinylene radical, such as an optionally substituted divalent 1,4-phenylene or a 2,5-pyridinylene radical of formula:

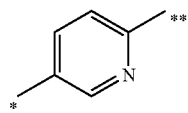

wherein the bond marked with a single asterisk is attached to $Ar^1$ and the bond marked with a double asterisk is attached to the oxygen shown in Formula (I).

Other specific examples of heteroarylene $Ar^3$ radicals include the following group of divalent radicals, any of which being optionally substituted:

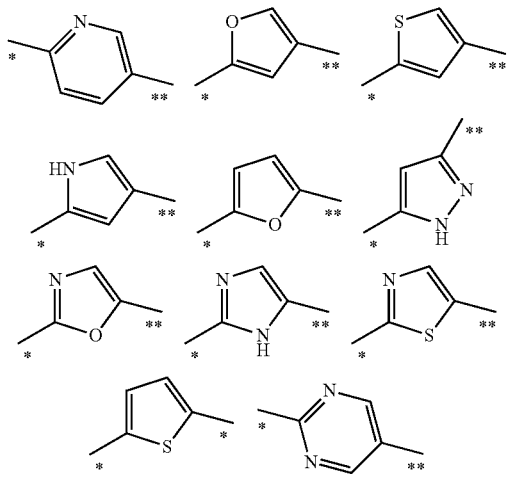

wherein the bond marked with a single asterisk is attached to $Ar^1$ and the bond marked with a double asterisk is attached to the oxygen.

Usually, no more than two optional substituents per ring will be present in $Ar^1$, $Ar^2$ and $Ar^3$. Any optional substituents in $Ar^1$, $Ar^2$ and $Ar^3$ may be independently selected from, for example, chloro, fluoro, bromo, cyclopropyl, methyl, mono-, di- or tri-methyl, trifluoromethyl, difluoromethyl, monofluoromethyl, methoxy, ethoxy, propoxy, butoxy, pentoxy, 2-methoxyethoxy, 2-benzyloxy-ethoxy, 2-hydroxy-ethoxy, mono-, di- or tri-fluoromethoxy, cyano, hydroxy, —$CO_2R$, or —$SO_2R_1$ wherein $R_1$ is hydrogen, methyl or ethyl, tetrazolyl, —$NR_2R_3$, —$CH_2NR_2R_3$ and —C(=O)$NR_2R_3$ wherein $R_2$ and $R_3$ are independently hydrogen, methyl or ethyl.

In some compounds of the invention the radical $Ar^1$-$Ar^3$— is 4-phenylphenyl, for example a biphenyl-4-yl radical.

In other compounds of the invention, $Ar^2$ is 2- or 3-fluorophenyl, or 3-pyridyl. In a currently preferred subclass of compounds of the invention:

$Ar^2$ is 3-pyridyl, pyrimidin-4-yl, pyrazin-2-yl or pyridazin-3-yl;

$Ar^3$ is an optionally substituted divalent 1,4-phenylene or a 2,5-pyridinylene radical of formula:

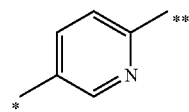

wherein the bond marked with a single asterisk is attached to $Ar^1$ and the bond marked with a double asterisk is attached to the oxygen; and $Ar^1$ is optionally substituted phenyl.

In that preferred subclass, $Ar^1$ may be, for example, 2-fluorophenyl, 3-(2-methoxy-ethoxy)-phenyl, or 2-methoxy-5-(2-methoxy-ethoxy)-phenyl, and it is currently preferred that $Ar^2$ be pyridazin-3-yl;

Specific examples of compounds of the invention include those of the Examples herein.

Compounds of the invention which are currently preferred for their combination of good intrinsic FAAH inhibitory potency, and high and prolonged plasma concentrations after oral administration, as evidenced in tests in laboratory rats, are 3-(biphenyl-4-yloxy)-azetidine-1-carboxylic acid pyridin-3-ylamide;

3-[5-(2-fluoro-phenyl)-pyridin-2-yloxy]-azetidine-1-carboxylic acid pyridazin-3-ylamide;

3-{5-[3-(2-methoxy-ethoxy)-phenyl]-pyridin-2-yloxy}-azetidine-1-carboxylic acid pyridazin-3-ylamide;

3-(5-phenyl-pyridin-2-yloxy)-azetidine-1-carboxylic acid pyridazin-3-ylamide;

3-[5-(2-methoxy-phenyl)-pyridin-2-yloxy]-azetidine-1-carboxylic acid pyridazin-3-ylamide;

and pharmaceutically acceptable salts thereof.

Synthesis

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to one skilled in the art. Typical literature sources are "Advanced organic chemistry", $4^{th}$ Edition (Wiley), J March, "Comprehensive Organic Transformation", $2^{nd}$ Edition (Wiley), R. C. Larock, "Handbook of Heterocyclic Chemistry", $2^{nd}$ Edition (Pergamon), A. R. Katritzky), review articles such as found in "Synthesis", "Acc. Chem. Res.", "Chem. Rev", or primary literature sources identified by standard literature searches online or from secondary sources such as "Chemical Abstracts" or "Beilstein". Such literature methods include those of the preparative Examples herein, and methods analogous thereto.

For example, an azetidine of formula (II) or a salt thereof may be reacted with an isocyanate of formula (III) to provide compounds of the invention. Any reactive optional substituents in $Ar^1$, $Ar^2$ or $Ar^3$ may be protected during the reaction and deprotected thereafter:

(II)

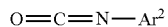
(III)

Other synthetic routes to compounds of the invention are summarized in Schemes 1, 2 and 3 of the Examples below.

Utilities

As stated above, the compounds of the invention are useful in the treatment of diseases or medical conditions which benefit from inhibition of FAAH activity, and examples of such diseases and conditions have been mentioned above.

It will be understood that the specific dose level for any particular patient will depend upon a variety of factors including the activity of the specific compound employed, the age, body weight, general health, sex, diet, time of administration, route of administration, rate of excretion, drug combination and the causative mechanism and severity of the particular disease undergoing therapy. In general, a suitable dose for orally administrable formulations will usually be in the range of 0.1 to 3000 mg, once, twice or three times per day, or the equivalent daily amount administered by injection, inhalation, infusion or other routes. However, optimum dose levels and frequency of dosing will be determined by clinical trials as is conventional in the art.

The compounds with which the invention is concerned may be prepared for administration by any route consistent with their pharmacokinetic properties. The orally administrable compositions may be in the form of tablets, capsules, powders, granules, lozenges, liquid or gel preparations. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents. Other particular formulations for oral administration include chewing gums, and suckable lozenges and lollipops, containing the compound of the invention.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia. Methods of delivery via sustained release patches for application to the skin are also known in the art.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The active ingredient may also be formulated for inhalation, for example as a nasal spray, or dry powder or aerosol inhalers. For delivery by inhalation, the active compound is preferably in the form of microparticles. They may be prepared by a variety of techniques, including spray-drying, freeze-drying and micronisation. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

Compounds of the invention may be administered together with other classes of pharmaceutically active drugs.

The following examples illustrate the preparation and activities of specific compounds of the invention and are not intended to be limiting of the full scope of the invention.

Part A: Examples 1-4

$^1$H (400 MHz) and $^{13}$C (100 MHz) Nuclear magnetic resonance (NMR) analysis was performed using a Bruker DPX-400 MHz NMR spectrometer. The spectral reference was the known chemical shift of the sample solvent. $^1$H nmr data is reported indicating the chemical shift ($\delta$), the multiplicity (s, singlet; d, doublet; t, triplet; q, quartet; m, multiplet; dd, doublet of doublets; br, broad; app, apparent etc.), the integration (e.g. 1H), the coupling constant(s) (J) in Hz. $^{13}$C data is reported indicating the chemical shift ($\square$). Deuterated solvents were obtained from the Sigma-Aldrich Chemical Company or Fluorochem.

LCMS analyses were performed on a HP1100 instrument, with a Luna 3 µM, C18(2), 30 mm×4.6 mm i.d. column from Phenomenex at a temperature of 22° C., at a flow rate of 2 mL min$^{-1}$ using the following solvent systems:

Solvent A: HPLC grade Water+10 mM ammonium acetate+0.08% v/v formic acid.
Solvent B: 95% v/v HPLC grade acetonitrile+5% v/v Solvent A+0.08% v/v formic acid.
Gradient: 95:5 Solvent A:Solvent B, 0.00 to 0.25 mins.; 95:5 to 5:95 Solvent A:Solvent B, 0.25 to 2.50 mins.; 5:95 Solvent A:Solvent B, 2.50 to 3.75 mins.

UV detection was at 230 nm, 254 nm and 270 nm. Mass spectrometer was a HP1100MSD, Series A instrument, operating in positive or negative ion electrospray ionisation mode. Molecular weight scan range is 120 to 1000. Samples were supplied as a 1 mM solution in DMSO, with 5 µL partial loop fill injection.

Preparative HPLC purifications were performed on a Waters FractionLynx MS Autopurification system with a Gemini® 5 µM C18(2), 100 mm×20 mm i.d. column from Phenomenex, running at a flow rate of 20 mL min$^{-1}$ with UV diode array detection (210-400 nm) and mass-directed collection. Gradients used for each compound are shown in Table 1. Solvents A and B are as for the analytical conditions above. The mass spectrometer was a Waters Micromass ZQ2000 spectrometer operating in positive or negative ion electrospray ionisation modes, with a molecular weight scan range of 150 to 1000.

Scheme A

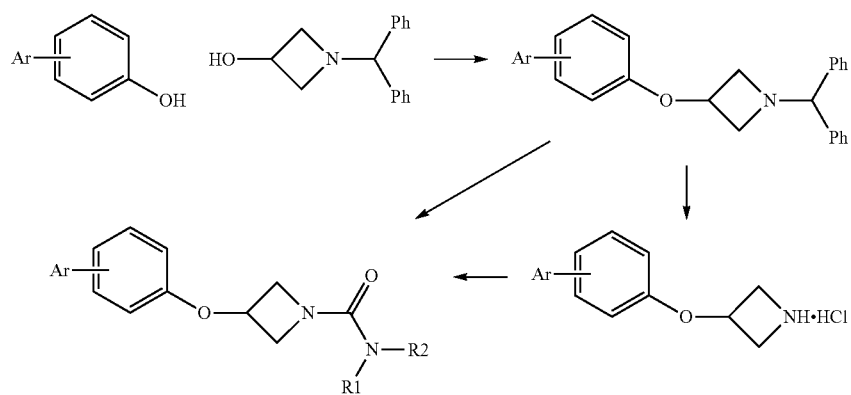

Example 1:
3-(biphenyl-4-yloxy)-azetidine-1-carboxylic acid phenylamide

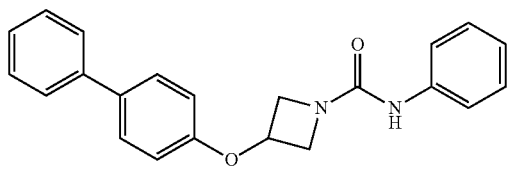

Step 1

1-Benzhydryl-3-(biphenyl-4-yloxy)azetidine

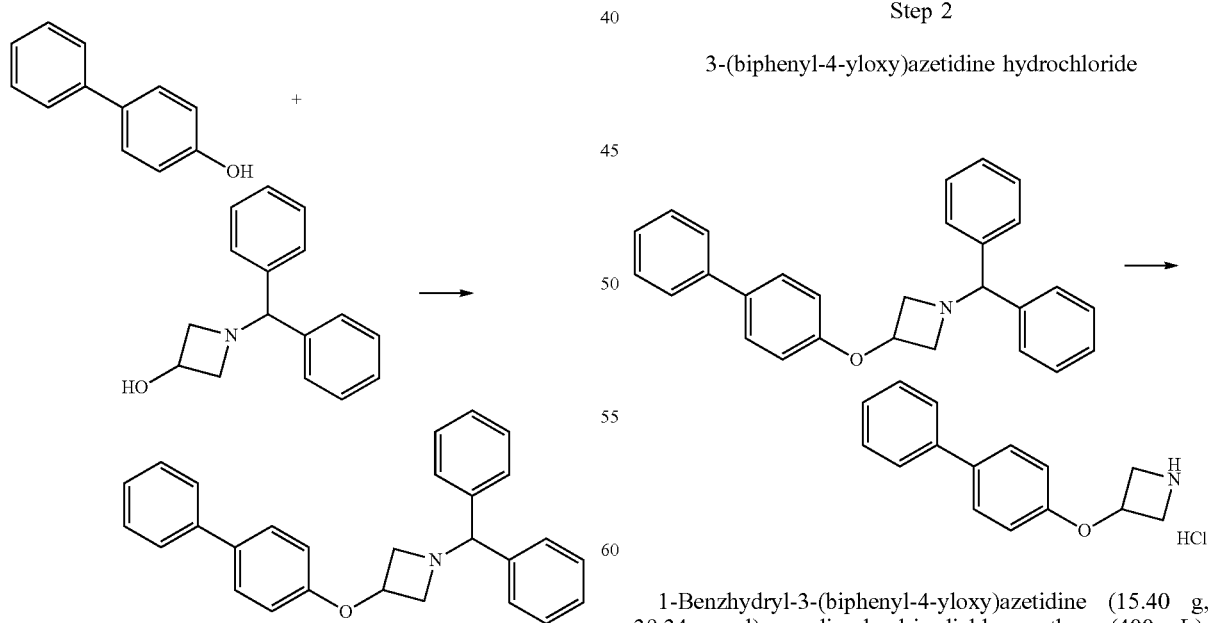

4-Phenylphenol (8.51 g, 50 mmol), 1-benzhydrylazetidin-3-ol (11.97 g, 50 mmol) and triphenylphosphine (13.11 g, 50 mmol) were stirred in acetonitrile (250 mL) for 20 minutes at room temperature, until all the reagents were fully dissolved. Diisopropyl Azodicarboxylate (9.84 mL, 10.11 g, 50 mmol) was added dropwise. A white precipitate forms and the initial reaction is mildly exothermic. The yellow colour is immediately discharged. After 5 minutes, the reaction is heated to reflux temperature, whereupon the precipitate dissolved, and stirred at this temperature for 3.25 hours. The mixture was cooled to room temperature, and scratched with a spatula to induce crystallisation. The mixture was cooled on ice, and the solids collected by filtration. The solids were washed with further cold acetonitrile and dried thoroughly to give the ether (15.42 g, 79%) as a white powder; mp 141-142° C.; $R_f$ 0.68 (2:1 hexane:EtOAc); LCMS retention time 2.57 mins, m/z 392.2 $[M+H]^+$; $^1H$ nmr (400 MHz; DMSO-$d_6$) δ 7.60-7.52 (m, 4H), 7.46-7.39 (m, 6H), 7.31-7.26 (m, 5H), 7.19 (tt, 2H, J=7.2 and 2.0 Hz), 6.90 (d, 2H, J=8.8 Hz), 4.88 (app qn, 1H, J=5.6 Hz), 4.53 (s, 1H), 3.67-3.63 (m, 2H) and 3.02-2.98 (m, 2H).

Step 2

3-(biphenyl-4-yloxy)azetidine hydrochloride

1-Benzhydryl-3-(biphenyl-4-yloxy)azetidine (15.40 g, 39.34 mmol) was dissolved in dichloromethane (400 mL), stirred, and cooled in an ice-water bath. 1-Chloroethyl chloroformate (8.49 mL, 11.25 g, 78.69 mmol) was added in 1 mL portions over 10 minutes, and the mixture stirred for a further 30 minutes at 0° C., then at rt for 25.5 hours.

Further 1-chloroethyl chloroformate (4.25 mL, 5.63 g, 39.35 mmol) was added and the mixture stirred for 3 days. The solvents were evaporated in vacuo and methanol (300 mL) added to the resulting white solid. The mixture was heated gently to dissolve, and then allowed to cool whilst stirring vigorously, whereupon a white precipitate formed. After a further 2 hours stirring at room temperature, the solids where collected by filtration to give the amine (7.41 g, 72%) as a white solid; mp>195° C.; LCMS retention time 1.64 mins, m/z 226.1 [M+H]$^+$; $^1$H nmr (400 MHz; DMSO-d$_6$) δ 9.26 (br s, 2H), 7.64-7.60 (m, 4H), 7.47-7.41 (m, 2H), 7.33 (ft, 1H, J=7.3 and 1.2 Hz), 6.96 (d, 2H, J=8.8 Hz), 5.13 (tt, 1H, J=6.8 and 4.8 Hz), 4.46 (dd, 2H, J=12.4 and 6.8 Hz) and 4.01 (dd, 2H, J=12.4 and 4.8 Hz).

Step 3: 3-(biphenyl-4-yloxy)-azetidine-1-carboxylic acid phenylamide

To a stirred suspension of 3-(1,1'-biphenyl-4-yloxy)azetidine hydrochloride (100 mg, 382 μmol) in dichloromethane (2.5 mL) was added triethylamine (63 μL, 48 mg, 478 μmol) followed by phenyl isocyanate (35 μL, 38 mg, 320 μmol) and the reaction stirred at room temperature for 2.5 hours. The mixture was loaded directly onto a 2 g prepacked SCX-2 cartridge and the product eluted with 1:1 dichloromethane:methanol (15 mL). The solvents were evaporated to give the urea (113 mg, 100%) as a white powder; LCMS retention time 2.57 minutes, m/z 345.2 [M+H]$^+$; $^1$H nmr (400 MHz; DMSO-d$_6$) δ 8.54 (s, 1H), 7.62 (d, 4H, J=7.6 Hz), 7.50 (d, 2H, J=8.0 Hz), 7.44 (t, 2H, J=7.6 Hz), 7.32 (t, 1H, J=7.2 Hz), 7.23 (t, 2H, J=7.8 Hz), 7.98-7.91 (m, 3H), 5.09 (m, 1H), 0.4.46-4.42 (m, 2H) and 3.95-3.91 (m, 2H).

Example 2: 3-(Biphenyl-4-yloxy)-azetidine-1-carboxylic acid (3-fluoro-phenyl)-amide

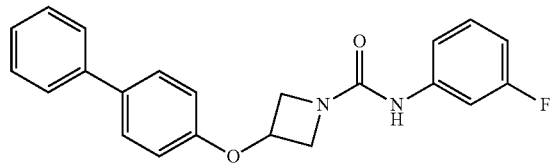 [SMILES: O=C(Nc1cccc(F)c1)N1CC(Oc2ccc(-c3ccccc3)cc2)C1]

The title compound was prepared as for Example 1, using 3-fluorophenyl isocyanate in place of phenyl isocyanate. The product was obtained as a white powder; LCMS retention time 2.61 minutes, m/z 363.1 [M+H]$^+$; $^1$H nmr (400 MHz; DMSO-d$_6$) δ 8.76 (s, 1H), 7.64-7.61 (m, 4H), 7.51-7.41 (m, 3H), 7.34-7.23 (m, 3H), 6.96 (d, 2H, J=8.4 Hz), 6.77-6.72 (m, 1H), 5.12-5.07 (m, 1H), 4.46 (dd, 2H, J=9.2 and 6.4 Hz) and 3.94 (dd, 2H, J=9.2 and 4.0 Hz).

Example 3: 3-(Biphenyl-4-yloxy)-azetidine-1-carboxylic acid (2-fluoro-phenyl)-amide

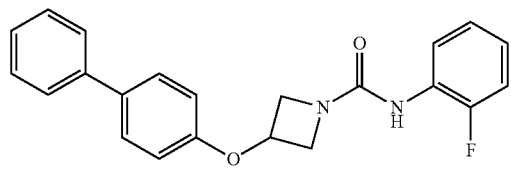 [SMILES: O=C(Nc1ccccc1F)N1CC(Oc2ccc(-c3ccccc3)cc2)C1]

The title compound was prepared as for Example 1, using 2-fluorophenyl isocyanate in place of phenyl isocyanate. The product was purified by trituration with diethyl ether to give the title compound as an off-white solid; LCMS retention time 2.60 minutes, m/z 363.1 [M+H]$^+$; $^1$H nmr (400 MHz; DMSO-d$_6$) δ 8.33 (s, 1H), 7.64-7.58 (m, 5H), 7.44 (t, 2H, J=7.6 Hz), 7.32 (t, 1H, J=7.4 Hz), 7.23-7.17 (m, 1H), 7.14-7.08 (m, 2H), 6.96 (d, 2H, J=8.8 Hz), 5.13-5.07 (m, 1H), 4.45 (dd, 2H, J=9.2 and 6.8 Hz) and 3.94 (dd, 2H, J=9.2 and 3.6 Hz).

Example 4: 3-(Biphenyl-4-yloxy)-azetidine-1-carboxylic acid pyridin-3-ylamide

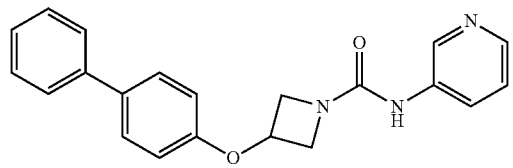 [SMILES: O=C(Nc1cccnc1)N1CC(Oc2ccc(-c3ccccc3)cc2)C1]

3-(Biphenyl-4-yloxy)azetidine hydrochloride (3 g, 11.47 mmol) was suspended in dichloromethane (45 mL) under a nitrogen atmosphere, treated with triethylamine (4.0 mL, 28.68 mmol) and stirred for 10 minutes at room temperature. The mixture was cooled to 0° C. and treated portionwise with pyridine-3-isocyanate (1.15 g, 9.56 mmol). Stirred at 0° C. for 10 minutes, then at rt for 16 hours. The solution was diluted with further dichloromethane (200 mL), washed with H$_2$O (2×100 mL), followed by brine (50 mL), dried (over MgSO$_4$), and solvent evaporated in vacuo to yield an off-white solid. The solid was triturated with diethyl ether, then stirred for 3 days with MP-isocyanate resin in a dichloromethane/methanol/acetonitrile mixture. The mixture was filtered and reduced to dryness in vacuo. The resulting solid was triturated successively with diethyl ether, then acetonitrile and filtered to give the urea (1.2 g, 36%) as a white solid; R$_f$ 0.10 (5% MeOH-DCM); LCMS retention time 2.08 minutes, m/z 346.2 [M+H]$^+$; $^1$H nmr (400 MHz; DMSO-d$_6$) δ 8.97 (s, 1H), 8.75 (d, 1H, J=2.3 Hz), 8.21 (d, 1H, J=4.7 Hz), 8.05-8.01 (m, 1H), 7.65-7.60 (m, 4H), 7.44 (t, 2H, J=7.9 Hz), 7.39 (dd, 1H, J=8.3 and 4.7 Hz), 7.32 (t, 1H, J=7.3 Hz), 6.96 (d, 2H, J=8.8 Hz), 5.14-5.08 (m, 1H), 4.49 (dd, 2H, J=9.5 and 6.5 Hz) and 3.97 (dd, 2H, J=9.5 and 3.8 Hz); $^{13}$C nmr (100 MHz; DMSO-d$_6$) 156.2 (C), 155.9 (C), 141.4 (CH), 139.6 (C), 138.9 (CH), 137.3 (C), 133.4 (C), 128.9 (CH), 128.1 (CH), 126.9 (CH), 126.8 (CH), 126.3 (CH), 123.9 (CH), 115.1 (CH), 65.6 (CH) and 56.4 (CH$_2$).

Part B—Examples 5-19

General Procedures

All reagents obtained from commercial sources were used without further purification. Anhydrous solvents were obtained from commercial sources and used without further drying. Flash chromatography was performed with prepacked silica gel cartridges (Strata SI-1; 61 Å, Phenomenex, Cheshire UK or IST Flash II, 54 Å, Argonaut, Hengoed, UK). Thin layer chromatography (TLC) was conducted with 5×10 cm plates coated with Merck Type 60 F$_{254}$ silica gel. Once visible under UV, the retention factor (R$_f$) value of each spot could be determined if appropriate by dividing the distance traveled by the product by the total distance traveled by the solvent (the solvent front).

Some compounds of the present invention were characterized by LC/MS (Method A) using a Hewlett Packard 1100 series LC/MSD linked to quadripole detector (ionization mode: electron spray positive or negative; column: Phenomenex Luna 3 μM C18(2) 30×4.6 mm at 22° C. Buffer A prepared by dissolving 1.93 g ammonium acetate in 2.5 L HPLC grade H$_2$O and adding 2 mL formic acid. Buffer B prepared by adding 132 mL buffer A to 2.5 L of HPLC grade acetonitrile and adding 2 mL formic acid; elution gradient 95:5 to 5:95 buffer A:buffer B over 3.75 minutes. (Injection volume: 2 μL). Flow rate=2.0 mL/min. UV detection was by diode array detector at 230, 254 and 270 nm. Retention Times (RT) are reported in minutes. Ionisation is positive unless otherwise stated.

Some compounds of the present invention were characterised by an alternative LC/MS method ("Method B") using an Agilent 1200 SL series instrument connected to an Agilent MSD 6140 single quadrupole with a multimode source; column: Phenomenex Luna 2.5 μM C18, 50×2 mm, HST at 55° C. column temperature. Buffer A: Water/10 mM ammonium formate/0.04% (v/v) formic acid pH=3.5. Buffer B: Acetonitrile/5.3% (v/v) A/0.04% (v/v) formic. Gradients and flow rates for method B are shown in Table 1 (Injection volume: 2 μL). UV detection was by diode array detector at 230, 254 and 270 nm. Retention Times (RT) are reported in minutes. Ionisation is positive unless otherwise stated.

TABLE 1

Solvent Gradients and Flow rates for LC/MS Method B.

| Time (min) | Solvent A (%) | Solvent B (%) | Flow (mL/min) |
|---|---|---|---|
| 0.00 | 95 | 5 | 1.1 |
| 0.12 | 95 | 5 | 1.1 |
| 1.30 | 5 | 95 | 1.1 |
| 1.35 | 5 | 95 | 1.7 |
| 1.85 | 5 | 95 | 1.7 |
| 1.90 | 5 | 95 | 1.1 |
| 1.95 | 95 | 5 | 1.1 |

Nuclear magnetic resonance (NMR) analysis was performed with a Brucker DPX-400 MHz NMR spectrometer. The spectral reference was the known chemical shift of the solvent. Proton NMR data is reported as follows: chemical shift (δ) in ppm, multiplicity (s=singlet, d=doublet, t=triplet, q=quartet, p=pentet, m=multiplet, dd=doublet of doublet, br=broad), integration, coupling constant.

Some compounds of the invention were purified by preparative HPLC. Preparative HPLC purifications were performed on a Waters FractionLynx MS Autopurification system with a Gemini® 5 μM C18(2), 100 mm×20 mm i.d. column from Phenomenex, running at a flow rate of 20 mL min$^{-1}$ with UV diode array detection (210-400 nm) and mass-directed collection. Appropriate solvents gradients for compound elution were determined for each particular compound.

At pH 4:
Solvent A: HPLC grade Water+10 mM ammonium acetate+0.08% v/v formic acid.
Solvent B: 95% v/v HPLC grade acetonitrile+5% v/v Solvent A+0.08% v/v formic acid.

At pH 9:
Solvent A: HPLC grade Water+10 mM ammonium acetate+0.08% v/v ammonia solution.
Solvent B: 95% v/v HPLC grade acetonitrile+5% v/v Solvent A+0.08% v/v ammonia solution.

$^1$H (400 MHz) and $^{13}$C (100 MHz) Nuclear magnetic resonance (NMR) analysis was performed using a Bruker DPX-400 MHz NMR spectrometer. The spectral reference was the known chemical shift of the sample solvent. $^1$H nmr data is reported indicating the chemical shift (δ), the multiplicity (s, singlet; d, doublet; t, triplet; q, quartet; m, multiplet; dd, doublet of doublets; br, broad; app, apparent etc.), the integration (e.g. 1H), the coupling constant(s) (J) in Hz. $^{13}$C data is reported indicating the chemical shift (□). Deuterated solvents were obtained from the Sigma-Aldrich Chemical Company or Fluorochem.

The mass spectrometer was a Waters Micromass ZQ2000 spectrometer operating in positive or negative ion electrospray ionisation modes, with a molecular weight scan range of 150 to 1000.

IUPAC chemical names were generated using AutoNom Standard.

Some compounds of the Examples were made by the route outlined in scheme 1.

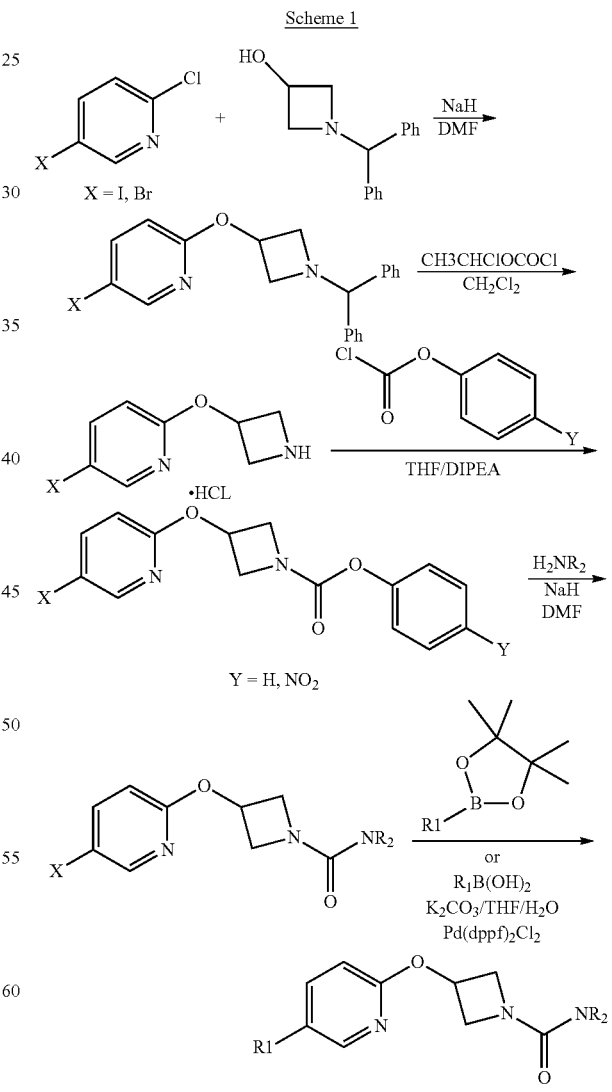

Some compounds of the Examples were made by the route outlined in scheme 2.

Scheme 2

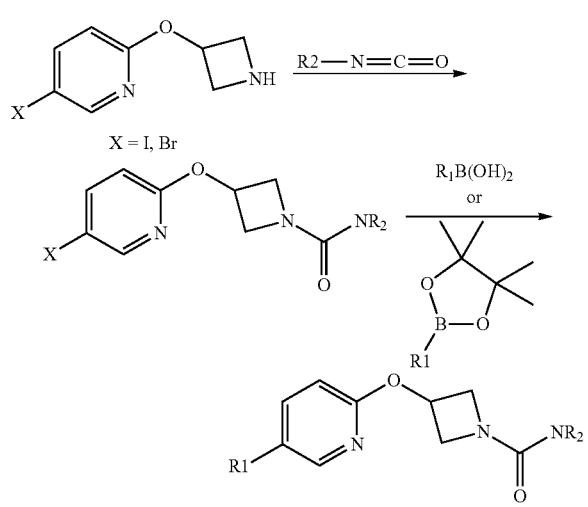

Some compounds of the Examples were made by the route outlined in scheme 3. Experimental methods, reagents and product isolation methods will be known to those skilled in the art of organic synthesis. It is understood that other methods can also be used.

Scheme 3

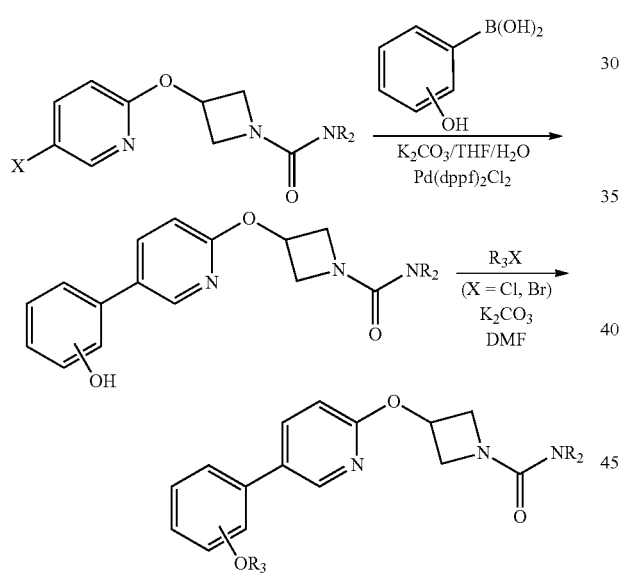

Example 5

3-{5-[3-(2-Methoxy-ethoxy)-phenyl]-pyridin-2-yloxy}-azetidine-1-carboxylic acid pyrimidin-4-ylamide

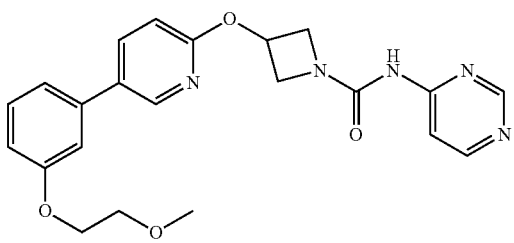 [SMILES: COCCOc1cccc(-c2ccc(OC3CN(C(=O)Nc4ccncn4)C3)nc2)c1]

Step 1

2-(1-Benzhydryl-azetidin-3-yloxy)-5-iodo-pyridine

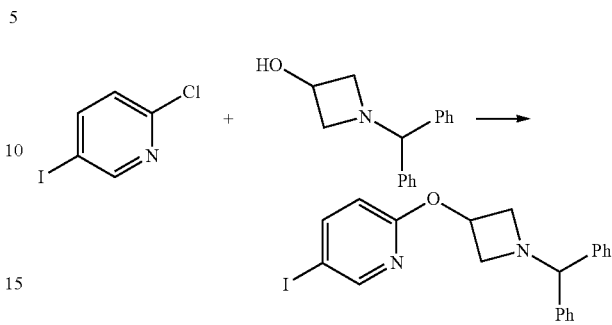

Sodium Hydride (60 wt % dispersion in mineral oil, 6.36 g, 0.156 mol) was added in portions to a solution of 1-benzhydryl-azetidin-3-ol (25.38 g, 0.106 mol) in anhydrous dimethylformamide (400 mL) under a Nitrogen atmosphere. This caused a precipitate to form and effervescence to occur. When addition was complete the reaction mixture was stirred at ambient temperature for 15 min. A solution of 2-chloro-5-iodopyridine (25.40 g, 0.106 mol) in dimethylformamide (100 mL) was added to the reaction mixture via a dropping funnel over 15 minutes. When addition was complete the reaction mixture was heated to 70° C. and stirred, under nitrogen atmosphere, for 4.5 hr. Reaction mixture was then allowed to cool to ambient temperature and a sat. aqueous ammonium chloride solution (30 mL) was added. The solvents were removed in vacuo and the residual solid was partitioned between ethyl acetate (600 mL) and sat. aqueous sodium bicarbonate solution (500 mL). The phases were separated and the organic phase was washed with sat. aqueous sodium chloride solution (3×300 mL), dried over sodium sulphate, filtered and filtrate solvents removed in vacuo to afford a yellow-brown solid which was triturated with diethyl ether, filtered and dried in vacuo to afford the title compound as a beige-coloured solid (33.41 g, 71%)

LCMS (Method A) RT=2.19 min; m/z=443 [M+H]$^+$

Step 2

2-(Azetidin-3-yloxy)-5-iodo-pyridine hydrochloride

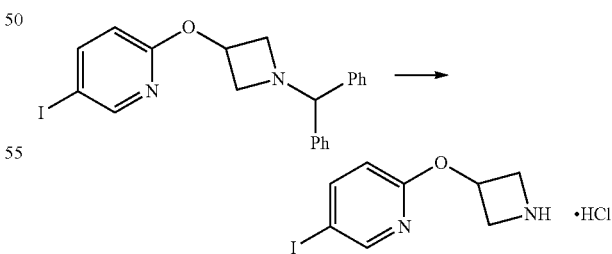

1-chloroethyl chloroformate (12.8 mL, 0.104 mol) was added drop-wise via syringe to a stirred solution of 2-(1-Benzhydryl-azetidin-3-yloxy)-5-iodo-pyridine (23.03 g, 0.052 mol) in dichloromethane (250 mL) at ambient temperature. The resulting solution was stirred at ambient temperature for 3.5 hr, then methanol (250 mL) was added and the reaction mixture stirred at ambient temperature for 16 hr. The solvents were then removed in vacuo and the resulting solid residue was triturated with diethyl ether, filtered and then dried in vacuo to afford the title product as a cream-coloured solid (17.8 g, >quant yield). The crude product was used directly without further purification.

LCMS (Method A) RT=1.24 min; m/z=277 [M+H]$^+$

Step 3

Intermediate 5

3-(5-Iodo-pyridin-2-yloxy)-azetidine-1-carboxylic acid 4-nitro-phenyl ester

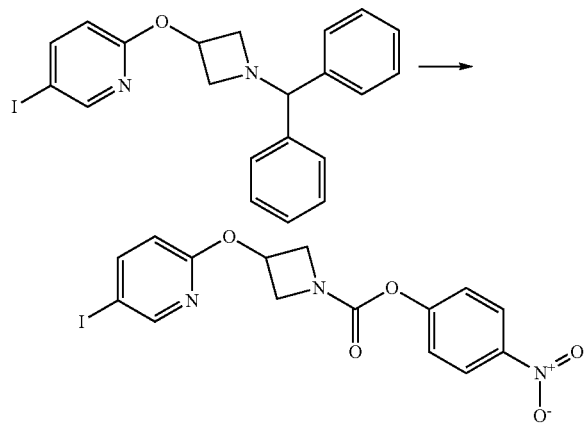

4-nitrophenyl chloroformate (692 mg g, 3.44 mmol) was added to a stirred solution of 2-(1-Benzhydryl-azetidin-3-yloxy)-5-iodo-pyridine (1.01 g, 2.29 mol) in dichloromethane (40 mL) at ambient temperature. The resulting solution was stirred at ambient temperature for 18 hr. The solvent was removed in vacuo and the product purified by flash chromatography on silica gel (25 g) eluting with dichloromethane to afford the title compound as a colourless solid (474 mg, 47%).

LCMS (Method A) RT=2.54 min; m/z=442 [M+H]$^+$. $^1$H NMR: (400 MHz, DMSO-d$_6$) δ 3.95-4.04 (m, 1H, 4.16-4.24 (m, 1H), 4.36-4.44 (m, 1H), 4.56-4.74 (m, 1H), 5.35-5.40*m, 1H), 6.84 (d, 1H, J=8.5 Hz), 7.43-7.47 (m, 2H), 8.07 (dd, 1H, J=8.5, 2.2 Hz), 8.26-8.29 (m, 2H), 8.38 (d, 1H, J=2.1 Hz).

Step 4

3-(5-iodo-pyridin-2-yloxy)-azetidine-1-carboxylic acid pyrimidin-4-ylamide

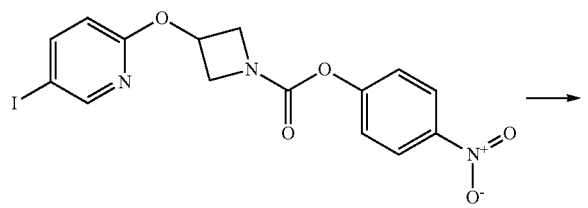

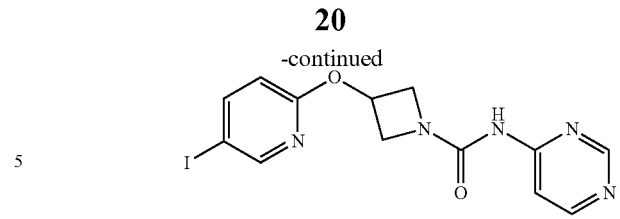

A solution of 4-aminopyrimidine (Aldrich, 243 mg, 2.54 mmol) in anhydrous DMF (4 mL) was added via syringe to a suspension of sodium hydride (60 wt % dispersion in mineral oil, 185 mg, 4.62 mmol) in anhydrous DMF (4 mL) under a nitrogen atmosphere. The mixture was stirred for 5 min. then a solution of 3-(5-Iodo-pyridin-2-yloxy)-azetidine-1-carboxylic acid 4-nitro-phenyl ester (1.02 g, 2.31 mmol) in anhydrous DMF (6 mL) was added drop-wise and the resulting yellow coloured turbid mixture was stirred at ambient temperature for 1.5 hr. The reaction mixture was poured into sat. aqueous ammonium chloride solution (30 mL) and extracted with ethyl acetate (3×100 mL). The combined organic phases were washed with sat. aqueous sodium chloride solution (100 mL) and dried over sodium sulphate. The mixture was filtered and the filtrate solvents removed in vacuo to afford a yellow solid, which was triturated with diethyl ether, filtered and dried to afford the title compound (594 mg, 65%) as a colourless solid.

LCMS (Method A) RT=1.89 min; m/z=398 [M+H]$^+$.

Step 5

2-[3-(2-Methoxy-ethoxy)-phenyl]-4,4,5,5-tetramethyl-[1,3,2]dioxaborolane

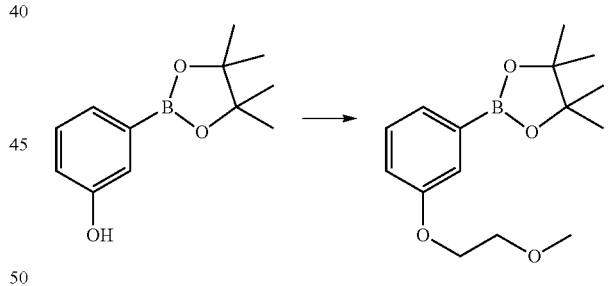

Potassium carbonate (1.88 g, 13.65 mmol) was added to a solution of 3-hydroxyphenylboronic acid pinacol ester (Apollo, 1.0 g, 4.55 mmol) in DMF (10 mL). 2-Bromoethyl methyl ether (0.41 mL, 5.46 mmol) was added and the reaction mixture was heated to 100° C. for 1 hr. The reaction mixture was allowed to cool and then partitioned between ethyl acetate (50 mL), and water (150 mL). The phases were separated and the organic phase was washed with brine (150 mL), dried over anhydrous sodium sulphate, filtered and the filtrate solvents removed in vacuo, to afford the title product as a light-brown oil (1.1 g) which was used without further purification.

LCMS (Method A) RT=1.42 min; m/z=no ionisation.

Step 6

3-{5-[3-(2-Methoxy-ethoxy)-phenyl]-pyridin-2-yloxy}-azetidine-1-carboxylic acid pyrimidin-4-ylamide

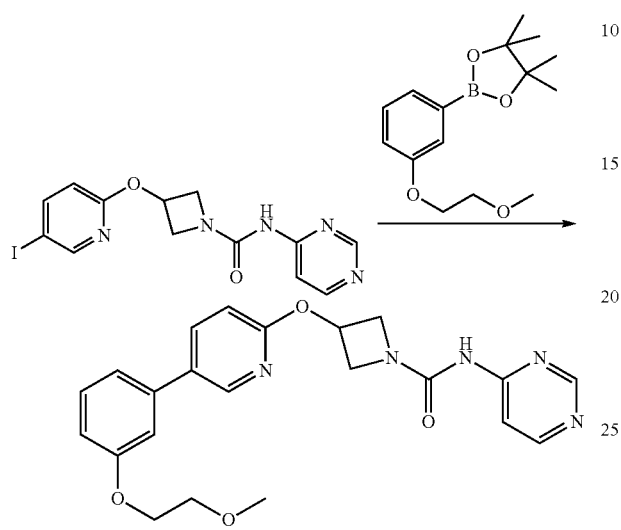

A solution of 2-[3-(2-Methoxy-ethoxy)-phenyl]-4,4,5,5-tetramethyl-[1,3,2]dioxaborolane (Step 5, 109 mg, 0.39 mmol) in THF/H$_2$O (10:1; 3 mL) was added to a microwave vial containing 3-(5-iodo-pyridin-2-yloxy)-azetidine-1-carboxylic acid pyrimidin-4-ylamide (step 4, 104 mg, 0.26 mmol) and potassium carbonate (108 mg, 0.786 mmol). Nitrogen gas was bubbled through the mixture for 5 mins then 1,1-bis[(diphenylphosphino)-ferrocene]dichloropalladium(II) complex with CH$_2$Cl$_2$ (21 mg, 10 mole %) was added and the vial sealed and heated at 100° C. in microwave synthesiser for 30 min. The cooled reaction mixture was diluted with ethyl acetate (20 mL) and washed through celite (2.5 g IST cartridge). A further 10 mL of ethyl acetate was washed through the celite pad and combined filtrate was washed sequentially with water (30 mL), 1N NaOH solution (30 mL), water (30 mL) then sat. sodium chloride solution (30 mL). Mixture dried over sodium sulphate and filtered. Filtrate solvents were removed in vacuo to afford a brown gum, which was purified by flash chromatography, eluting with a gradient of 50 to 100% ethyl acetate in hexane to a afford a gummy solid. Product was dissolved in dichloromethane (25 mL) and 2N NaOH (aq, 25 mL) was added and mixture stirred vigorously for 1 h. Phases were separated and the organic layer dried over sodium sulphate, filtered and filtrate solvent removed in vacuo to leave a solid, which was triturated with diethyl ether, filtered and dried to afford the title compound as colourless solid (50 mg, 45%)

LCMS: (Method A) RT=1.97 min; m/z=422 [M+H]$^+$.

TLC: R$_f$=0.39 (100% EtOAc). $^1$H NMR: (400 MHz, DMSO-d$_6$) δ 3.32 (s, 3H), 3.68 (m, 2H), 4.03 (brm, 2H), 4.17 (m, 2H), 4.48 (brm, 2H), 5.38 (m, 1H), 6.95 (dd, 1H, J=8.1, 2.5 Hz), 6.99 (d, 1H, J=8.6 Hz), 7.20-7.26 (m, 2H), 7.37 (dd, 1H, J=8.3, 8.3 Hz), 7.92 (dd, 1H, J=5.7, 1.2 Hz), 8.08 (dd, 1H, J=8.6, 2.5 Hz), 8.48-8.54 (m, 2H), 8.57 (m, 1H), 9.86 (brs, 1H).

Example 6

3-{5-[3-(2-Methoxy-ethoxy)-phenyl]-pyridin-2-yloxy}-azetidine-1-carboxylic acid pyrazin-2-ylamide

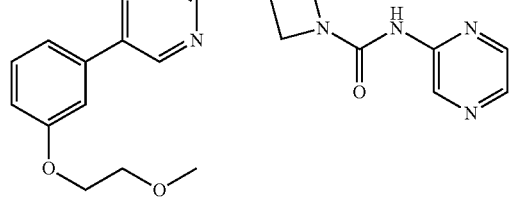

Step 1

2-(1-Benzhydryl-azetidin-3-yloxy)-5-bromo-pyridine

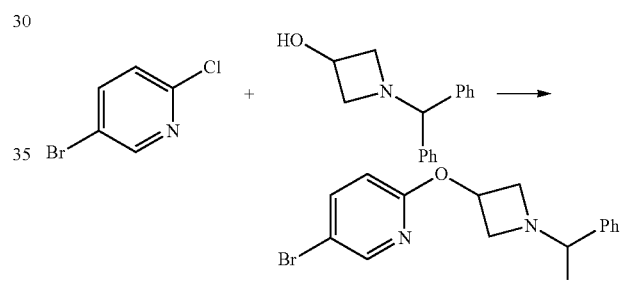

This compound was prepared by the method outlined for example 5 step 1. Thus 5-bromo-2-chloropyridine (31.31 g, 0.163 mol) and 1-benzhydryl-azetidin-3-ol (38.92 g, 0.163 mol) were reacted to afford title compound (44.14 g, 64%) as light brown solid.

LCMS: (Method A) RT=2.11 min; m/z=397 [M+H]$^+$.

Step 2

2-(Azetidin-3-yloxy)-5-bromo-pyridine hydrochloride

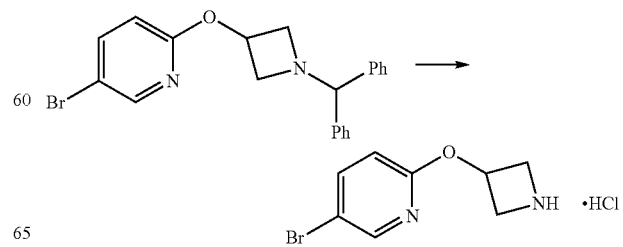

This compound was prepared by the method outlined for example 5 step 2. Thus 2-(Azetidin-3-yloxy)-5-bromo-pyridine hydrochloride (13.76 g, 0.035 mole) was reacted with 1-chloroethyl chloroformate to afford title compound (10.22 g>quant. yield) as a brown solid.

LCMS: (Method A) RT=1.15 min; m/z=231 [M+H]+.

Step 3

3-(5-Bromo-pyridin-2-yloxy)-azetidine-1-carboxylic acid 4-nitro-phenyl ester

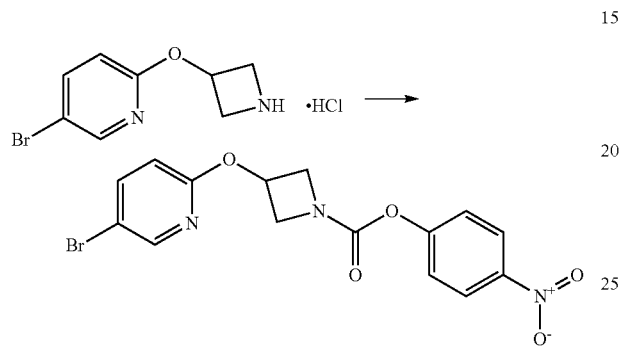

This compound was prepared by the method outlined for example 5 step 3. Thus 2-(Azetidin-3-yloxy)-5-bromo-pyridine hydrochloride (2.0 g, 7.53 mmol) was reacted with 4-nitrophenyl chloroformate to afford the title compound (1.11 g, 37%) as a pale-yellow solid.

LCMS: (Method A) RT=2.50 min; m/z=396 [M+H]+.

Step 4

3-(5-bromo-pyridin-2-yloxy)-azetidine-1-carboxylic acid pyrazin-2-ylamide

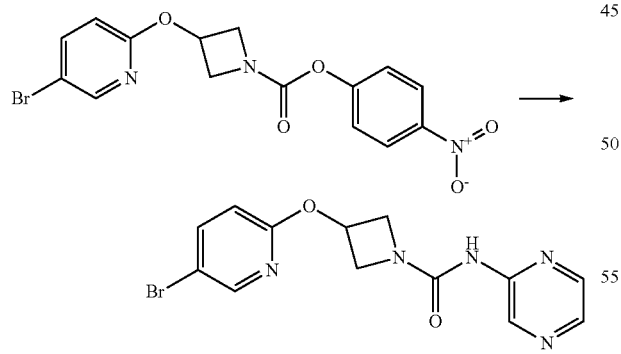

This compound was prepared by the method outlined for example 5 step 4. Thus 3-(5-bromo-pyridin-2-yloxy)-azetidine-1-carboxylic acid 4-nitro-phenyl ester (905 mg, 2.30 mmol) was reacted with 2-aminopyrazine (243 mg, 2.53 mmol) to afford the title compound (454 mg, 56%) as off white solid.

LCMS: (Method A) RT=1.86 min; m/z=352 [M+H]+.

Step 5

3-{5-[3-(2-Methoxy-ethoxy)-phenyl]-pyridin-2-yloxy}-azetidine-1-carboxylic acid pyrazin-2-ylamide

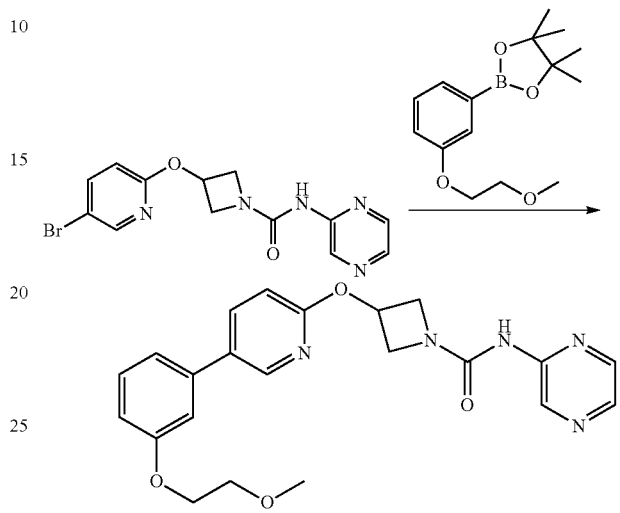

This compound was prepared by the method outlined for example 5 step 6. Thus 3-(5-bromo-pyridin-2-yloxy)-azetidine-1-carboxylic acid pyrazin-2-ylamide (100 mg, 0.285 mmol) was reacted with 2-[3-(2-Methoxy-ethoxy)-phenyl]-4,4,5,5-tetramethyl-[1,3,2]dioxaborolane (example 5 step 5, 118 mg, 0.855 mmol) to afford title compound (70 mg, 58%) as a colourless powder.

LCMS: (Method A) RT=2.01 min; m/z=422 [M+H]+.

TLC: $R_f$=0.51 (100% EtOAc)

$^1$H NMR: (400 MHz, DMSO-$d_6$) δ 3.32 (s, 3H), 3.68 (m, 2H), 4.03 (m, 2H), 4.17 (m, 2H), 4.48 (m, 2H), 5.39 (m, 1H), 6.95 (m, 1H), 6.99 (d, 1H, J=8.6 Hz), 7.21-7.25 (m, 2H), 7.37 (dd, 1H, J=8.3, 8.3 Hz), 8.09 (dd, 1H, J=8.5, 2.5 Hz), 8.22 (d, 1H, J=2.5 Hz), 8.29 (m, 1H) 8.49 (d, 1H, J=2.0 Hz), 9.17 (d, 1H, J=1.5 Hz), 9.65 (brs, 1H).

Example 7

3-{5-[3-(2-Methoxy-ethoxy)-phenyl]-pyridin-2-yloxy}-azetidine-1-carboxylic acid pyridazin-3-ylamide

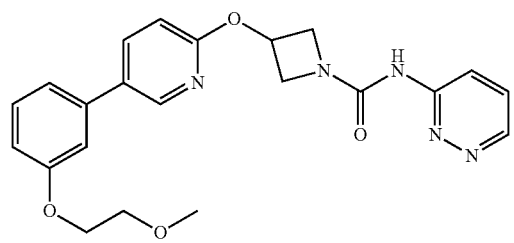 [SMILES: COCCOc1cccc(-c2ccc(OC3CN(C(=O)Nc4cccnn4)C3)nc2)c1]

Step 1

3-(5-iodo-pyridin-2-yloxy)-azetidine-1-carboxylic acid pyridazin-3-ylamide

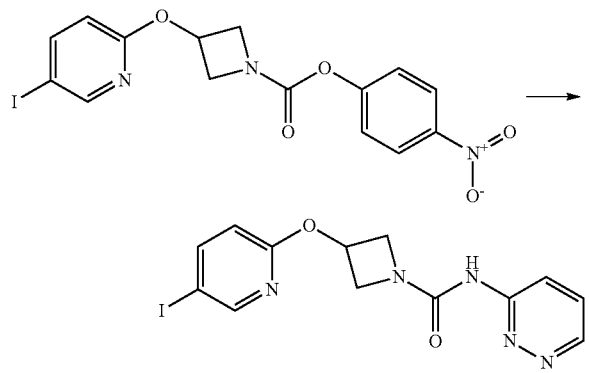

To an ice-bath cooled solution of sodium hydride (60 wt % in mineral oil, (2.1 g, 52.4 mmol) in DMF (50 mL) under nitrogen atmosphere was added (dropwise) a solution of 3-aminopyridazine (2.74 g, 28.79 mmol) in DMF (50 mL). After several minute a solution of 3-(5-iodo-pyridin-2-yloxy)-azetidine-1-carboxylic acid 4-nitro-phenyl ester (Example 5, step 3); 11.54 g, 26.18 mmol) in DMF (40 mL) was added. After 5 min the cooling bath was removed and reaction allowed to warm to ambient temperature and stir for 1.5 hr. Saturated sodium bicarbonate solution (500 mL) was added and the mixture was extracted with EtOAc (4×400 mL). Combined organic phases were washed with sat sodium chloride solution (500 mL), dried over sodium sulphate and filtered. The filtrate solvents were removed in vacuo to afford a crude product that was triturated with diethyl ether to afford the title compound (7.52 g, 72%) as a colourless solid.

LCMS: (Method A) RT=1.84 min; m/z=398 [M+H]$^+$.

Step 2

3-{5-[3-(2-Methoxy-ethoxy)-phenyl]-pyridin-2-yloxy}-azetidine-1-carboxylic acid pyridazin-3-ylamide

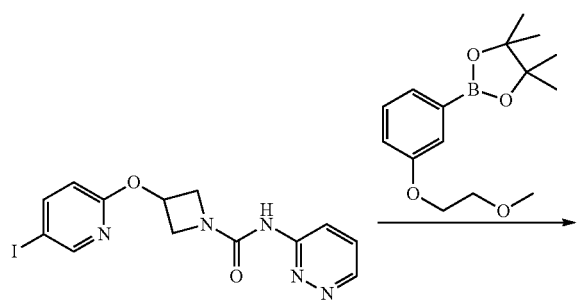

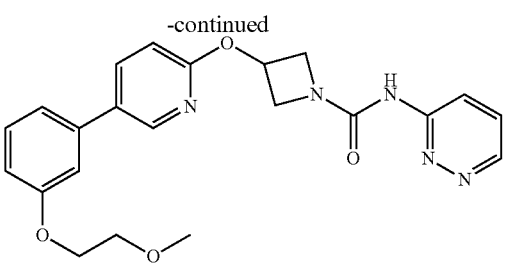

This compound was prepared in similar fashion to the method outlined for Example 5 step 6. Thus 3-(5-iodo-pyridin-2-yloxy)-azetidine-1-carboxylic acid pyridazin-3-ylamide (456 mg, 1.15 mmol) was reacted with 2-[3-(2-Methoxy-ethoxy)-phenyl]-4,4,5,5-tetramethyl-[1,3,2]dioxaborolane (example 5 step 5, 392 mg, 1.50 mmol) to afford title compound (120 mg, 25%) as a colourless powder.

LCMS: (Method A) RT=1.18 min; m/z=422 [M+H]+.

$^1$H NMR: (400 MHz, DMSO-d$_6$) δ 3.32 (s, 3H), 3.68 (m, 2H), 4.04 (brm, 2H), 4.17 (m, 2H), 4.49 (brm, 2H), 5.40 (m, 1H), 6.95 (m, 1H), 6.99 (d, 1H, J=8.9 Hz), 7.21-7.25 (m, 2H), 7.37 (dd, 1H, J=8.3, 8.3 Hz), 7.59 (dd, 1H, J=9.1, 4.5 Hz), 8.09 (dd, 1H, J=8.6, 2.6 Hz), 8.15 (dd, 1H, J=9.1, 1.4 Hz), 8.50 (d, 1H, J=4.5, 1.4 Hz), 8.85 (dd, 1H, J=4.5, 1.4 Hz), 9.97 (s, 1H).

Example 8

3-{5-[3-(2-Methoxy-ethoxy)-phenyl]-pyridin-2-yloxy}-azetidine-1-carboxylic acid pyridin-3-ylamide

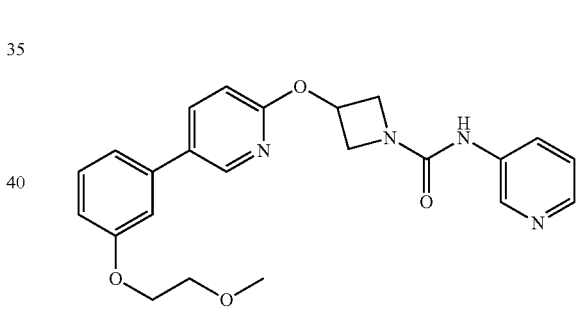

Step 1

3-(5-Iodo-pyridin-2-yloxy)-azetidine-1-carboxylic acid pyridin-3-ylamide

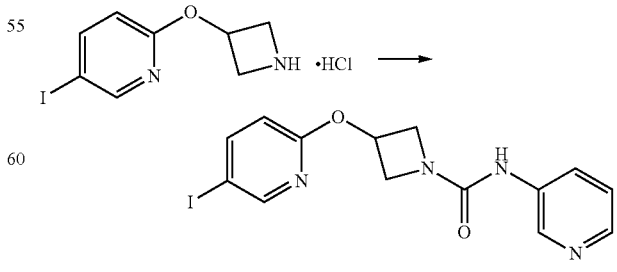

2-(Azetidin-3-yloxy)-5-iodo-pyridine hydrochloride (4.2 g, 13 mmol) was suspended in anhydrous dichloromethane (50 mL) and triethylamine (5.5 mL) was added. Pyridine-3-isocyanate (1.45 g, 11.7 mmol) was added and the reaction mixture was stirred at ambient temperature for 16 hr. The suspension solvents were removed in vacuo and the residue partitioned between ethyl acetate (400 mL) and sat. aqueous sodium bicarbonate solution (400 mL). The mixture was filtered through a pad of celite and the filtrate phases were separated. The organic phase was washed with sat. aqueous sodium bicarbonate solution (250 mL), then sat aqueous sodium chloride solution (250 mL) and dried over sodium sulphate and filtered. The filtrate solvents were removed in vacuo to afford a yellow solid which was purified by flash chromatography on silica gel (100 g), eluting with a 1:19 mix of 7N ammonia in methanol solution:dichloromethane. This affords the title compound (2.0 g, 42%) as a colourless solid.

LCMS: (Method A) RT=1.04 min; m/z=397 [M+H]$^+$.

Step 2

3-[5-(3-Hydroxy-phenyl)-pyridin-2-yloxy]-azetidine-1-carboxylic acid pyridin-3-ylamide

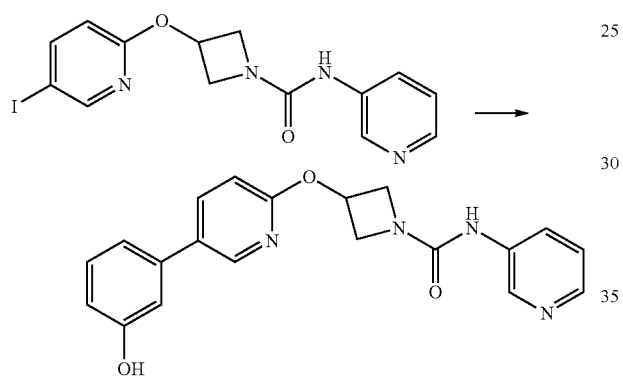

This compound was prepared by the method outlined for example 5 step 6. Thus 3-(5-iodo-pyridin-2-yloxy)-azetidine-1-carboxylic acid pyridin-3-ylamide (300 mg, 0.76 mmol) was reacted with 3-hydroxyphenylboronic acid (156 mg, 1.14 mmol) to afford a crude product purified by flash chromatography on silica gel eluting with solvent gradient of 1:19 to 1:9 7N ammonia in methanol solution:dichloromethane. This affords the title compound (130 mg, 47%) as a colourless powder.

LCMS: (Method A) RT=0.97 min; m/z=363 [M+H]$^+$.

Step 3

3-{5-[3-(2-Methoxy-ethoxy)-phenyl]-pyridin-2-yloxy}-azetidine-1-carboxylic acid pyridin-3-ylamide

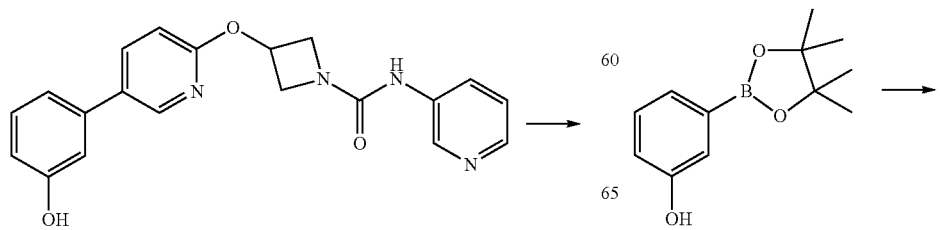

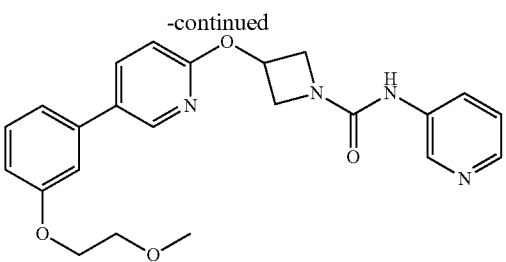

Potassium carbonate (23 mg, 165 µmop was added to a solution of 3-[5-(3-hydroxy-phenyl)-pyridin-2-yloxy]-azetidine-1-carboxylic acid pyridin-3-ylamide (20 mg 55 µmol), in DMF (0.5 mL). 2-Bromoethyl methyl ether (6 µL, 66 µmol) was added and the reaction mixture was heated to 100° C. in microwave synthesiser for 1 hr. The reaction mixture was allowed to cool and solvent removed in vacuo. The crude product was purified by preparative HPLC to afford the title product as a colourless solid (6.7 mg, 29%).

LCMS: (Method A) RT=1.11 min; m/z=421 [M+H]$^+$.

$^1$H NMR: (400 MHz, DMSO-d$_6$) δ 3.32 (s, 3H), 3.68 (m, 2H), 3.99 (m, 2H), 4.17 (m, 2H), 4.44 (m, 2H), 5.39 (m, 1H), 6.92-6.97 (m, 1H), 7.00 (d, 1H, J=8.6 Hz), 7.21-7.25 (m, 2H), 7.27 (dd, 1H, J=8.3, 4.8 Hz), 7.37 (dd, 1H, J=8.1, 8.1 Hz), 7.93 (dm, 1H), 8.09 (dd, 1H, J=8.6, 2.6 Hz), 8.15 (dd, 1H, J=4.5, 1.6 Hz), 8.49, (d, 1H, J=2.1 Hz), 8.66 (d, 1H, J=2.1 Hz), 8.75 (s, 1H).

Example 9

3-{5-[3-(2-Benzyloxy-ethoxy)-phenyl]-pyridin-2-yloxy}-azetidine-1-carboxylic acid pyridazin-3-ylamide

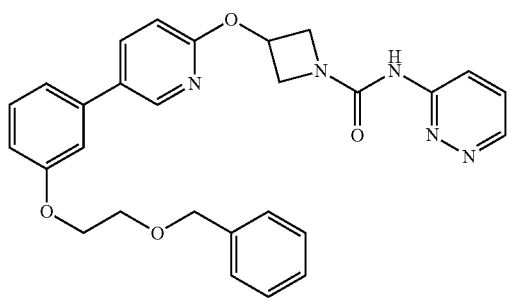 [SMILES: O=C(Nc1cccnn1)N1CC(Oc2ccc(-c3cccc(OCCOCc4ccccc4)c3)cn2)C1]

Step 1

2-[3-(2-Benzyloxy-ethoxy)-phenyl]-4,4,5,5-tetramethyl-[1,3,2]dioxaborolane

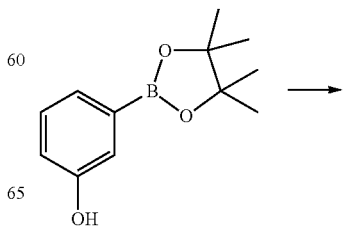

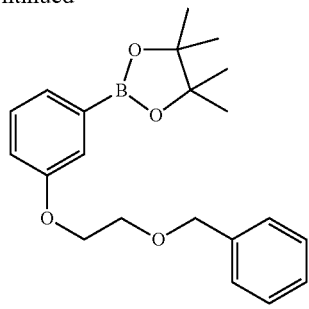

This compound was prepared by the method outlined for example 5 step 5. Thus 3-hydroxyphenylboronic acid pinacol ester (500 mg, 2.27 mmol) was reacted with benzyl-2-bromoethyl ether (0.54 mL, 3.41 mol) and the crude product after work up used without further purification.

Step 2

3-{5-[3-(2-Benzyloxy-ethoxy)-phenyl]-pyridin-2-yloxy}-azetidine-1-carboxylic acid pyridazin-3-ylamide This compound was prepared by the method outlined for example 5 step 6. Thus 3-(5-iodo-pyridin-2-yloxy)-azetidine-1-carboxylic acid pyridazin-3-ylamide (example 7, step 1) (600 mg, 1.15 mmol) was reacted with 2-[3-(2-benzyloxy-ethoxy)-phenyl]-4,4,5,5-tetramethyl-[1,3,2]dioxaborolane (1.5 equiv). Crude product purified by flash chromatography on silica gel eluting with 4:1 ethyl acetate: hexane to afford title compound (214 mg, 28%) as a brown foam.

LCMS: (Method B) RT=1.37 min; m/z=498 [M+H]$^+$.

$^1$H NMR: (400 MHz, DMSO-$d_6$) δ 3.80 (m, 2H), 4.04 (m, 2H), 4.23 (m, 2H), 4.49 (m, 2H), 4.57 (s, 2H), 5.40 (m, 1H), 6.96 (m, 1H), 6.99 (d, 1H, J=8.6 Hz), 7.21-7.25 (m, 2H), 7.29 (m, 1H), 7.33-7.39 (m, 5H), 7.59 (dd, 1H, J=9.1, 4.8 Hz), 8.08 (dd, 1H, J=8.6, 2.5 Hz), 8.15 (dd, 1H, J=9.1, 1.3 Hz), 8.49 (d, 1H, J=2.5 Hz), 8.84 (dd, 1H, J=4.5, 1.3 Hz), 9.97 (brs, 1H).

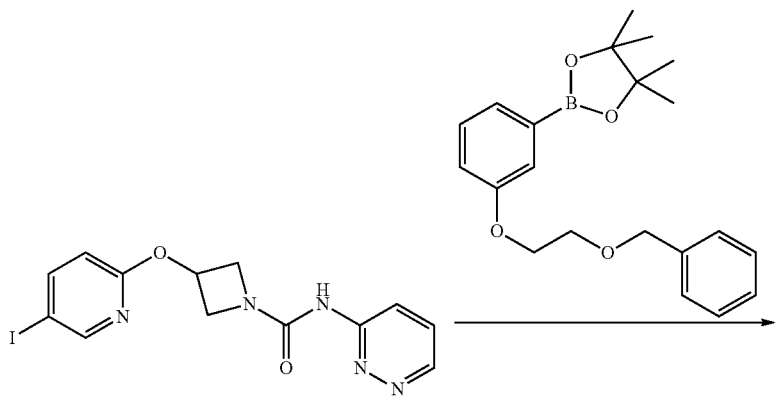

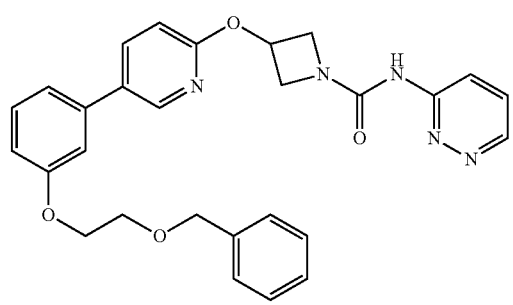

Example 10

3-{5-[3-(2-Hydroxy-ethoxy)-phenyl]-pyridin-2-yloxy}-azetidine-1-carboxylic acid pyridazin-3-ylamide

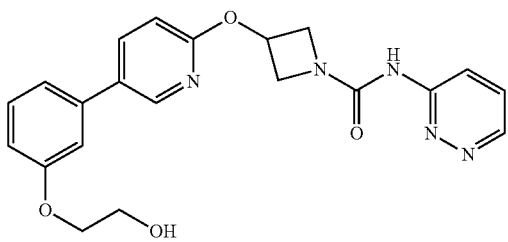 [SMILES: O=C(Nc1cccnn1)N1CC(Oc2ccc(-c3cccc(OCCO)c3)cn2)C1]

Step 1

3-{5-[3-(2-Hydroxy-ethoxy)-phenyl]-pyridin-2-yloxy}-azetidine-1-carboxylic acid pyridazin-3-ylamide

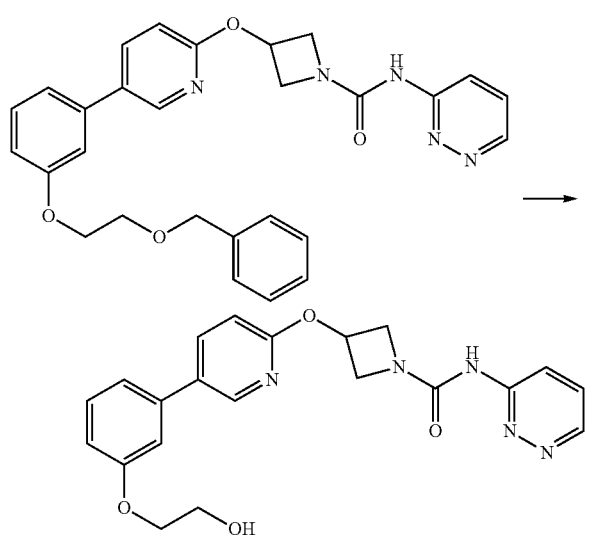

3-{5-[3-(2-Benzyloxy-ethoxy)-phenyl]-pyridin-2-yloxy}-azetidine-1-carboxylic acid pyridazin-3-ylamide (Example 9, 325 mg, 0.65 mmol) was dissolved in anhydrous dichloromethane (10 mL) under a nitrogen atmosphere. The mixture was cooled with an ice water bath and boron tribromide in dichloromethane solution (1M, 0.98 mL, 0.98 mmol) was added drop-wise affording a precipitate. The reaction mixture was stirred at 0° C. for 2 hr. The precipitate was collected by filtration and purified by flash chromatography on silica gel eluting with ethyl acetate, then 5-10% methanol in DCM. Further purification by preparative HPLC at pH4 afforded title compound (13 mg, 5%) as colourless solid.

LCMS: (Method B) RT=1.05 min; m/z=408 [M+H]$^+$.

$^1$H NMR: (400 MHz, DMSO-d$_6$) δ 3.73 (m, 2H), 4.00-4.09 (m, 4H), 4.49 (m, 2H), 4.89 (t, 1H, J=5.5 Hz), 5.40 (m, 1H), 6.94 (dm, 1H), 7.00 (d, 1H, J=8.6 Hz), 7.20-7.25 (m, 2H), 7.37 (dd, 1H, J=8.1, 8.1 Hz), 7.58 (dd, 1H, J=9.1, 4.8 Hz), 8.08 (dd, 1H, J=8.6, 2.8 Hz), 8.15 (dd, 1H, J=8.8, 1.2 Hz), 8.49 (d, 1H, J=1.7 Hz), 8.84 (dd, 1H, J=4.8, 1.7 Hz), 9.97 (brs, 1H).

Example 11

3-{5-[2-Methoxy-5-(2-methoxy-ethoxy)-phenyl]-pyridin-2-yloxy}-azetidine-1-carboxylic acid pyridazin-3-ylamide

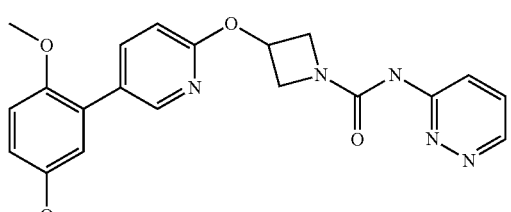

Step 1

Acetic acid 4-methoxy-phenyl ester

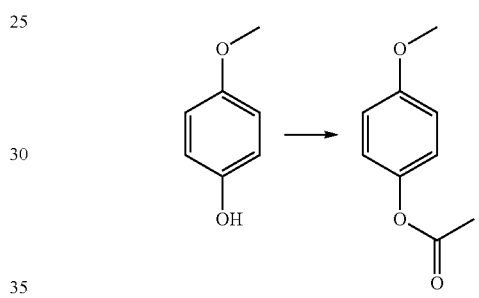

Triethylamine (14.55 mL, 104.43 mmol) was added to an ice-bath cooled solution of 4-methoxyphenol (5.185 g, 41.77 mmol) in anhydrous ether (200 mL) under nitrogen atmosphere. Acetyl chloride (5.94 mL, 83.53 mmol) was added drop-wise and reaction mixture then allowed to warm to room temperature and stir for a further 10 min. The reaction mixture was partitioned between ethyl acetate and sat aqueous sodium bicarbonate solution. The phases were separated and the organic phase was dried over sodium sulphate, filtered and filtrate solvents removed in vacuo to afford the title compound (7.45 g, quant) as a brown liquid.

LCMS: (Method A) RT=1.88 min; no ionisation.

TLC: R$_f$=0.72 (7:3 EtOAc:Hexane)

Step 2

Acetic acid 3-bromo-4-methoxy-phenyl ester

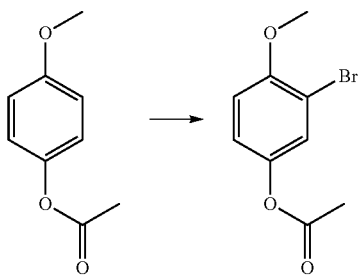

Acetic acid (2.24 mL, 7.4 mmol) was added to a mixture of acetic acid 4-methoxy-phenyl ester (1.0 g, 6.02 mmol) and sodium acetate (940 mg, 11.46 mmol). A solution of bromine (0.37 mL, 6.02 mmol) in acetic acid (2.1 mL) was added drop-wise and mixture stirred for 18 hr at ambient temperature. A further 0.6 mL of acetic acid was added followed by a further 0.1 mL of bromine. Mixture was stirred for 2 hours, then partitioned between ethyl acetate (100 mL) and water (100 mL). The phases were separated and organic layer was washed sequentially with sat. aqueous sodium bicarbonate solution (2×150 mL), sat. aqueous sodium thiosulphate solution (100 mL) and sat. aqueous sodium chloride solution (100 mL). Organic phase was dried over sodium sulphate, filtered and filtrate solvents removed in vacuo to afford a oil which was purified by flash chromatography on silica gel, eluting with a gradient of 0-10% ethyl acetate in hexane to afford title compound (1.2 g, 81%) as a light-brown oil.

LCMS: (Method A) RT=2.11 min; no ionisation.
TLC: $R_f$=0.20 (1:9 EtOAc:Hexane)

Step 3

3-Bromo-4-methoxy-phenol

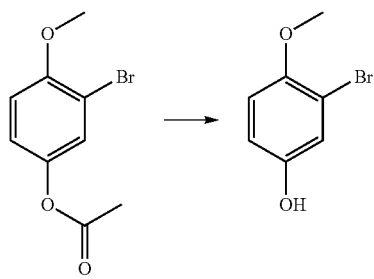

A solution of potassium hydroxide (290 mg, 5.19 mmol) in water (2.5 mL) was added to a solution of acetic acid 3-bromo-4-methoxy-phenyl ester (1.2 g, 4.9 mmol) in methanol (18.5 mL). Mixture was stirred at ambient temperature for 30 min, then solvents were removed in vacuo and water (40 mL) added. The mixture was made acidic by drop-wise addition of 1.2 M aq HCl solution (4.3 mL) and the mixture extracted with dichloromethane (2×40 mL). Combined organics were dried over sodium sulphate, filtered and filtrate solvents evaporated in vacuo to give the title compound (976 mg, 98%) as a pale yellow solid.

LCMS: (Method A) RT=2.11 min; no ionisation
TLC: $R_f$=0.28 (1:4 EtOAc:Hexane)

Step 4

2-Bromo-1-methoxy-4-(2-methoxy-ethoxy)-benzene

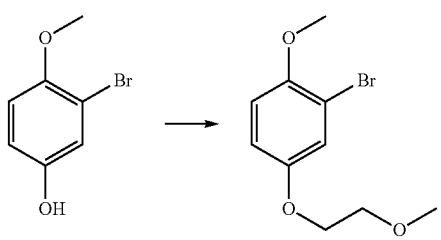

2-bromoethyl methyl ether (0.07 mL, 0.74 mmol) was added to a mixture of potassium carbonate (136 mg, 0.99 mmol) and 3-bromo-4-methoxy-phenol (100 mg, 0.49 mmol) in DMF (2 mL) and mix heated at 100° C. for 1 hr. Reaction mixture was allowed to cool and partitioned between ethyl acetate (20 mL×2) and water (20 mL). The combined organic phases were washed with sat. aqueous sodium chloride solution (40 mL) and dried over sodium sulphate. Solvents were removed in vacuo to afford a crude oil which was purified by flash chromatography on silica gel, eluting with a gradient of 0-10% ethyl acetate in hexane to afford the title compound (113 mg, 88%) as a colourless liquid.

LCMS: (Method A) RT=2.12 min; no ionisation.
TLC: $R_f$=0.34 (1:4 EtOAc:Hexane)

Step 5

3-{5-[2-Methoxy-5-(2-methoxy-ethoxy)-phenyl]-pyridin-2-yloxy}-azetidine-1-carboxylic acid pyridazin-3-ylamide

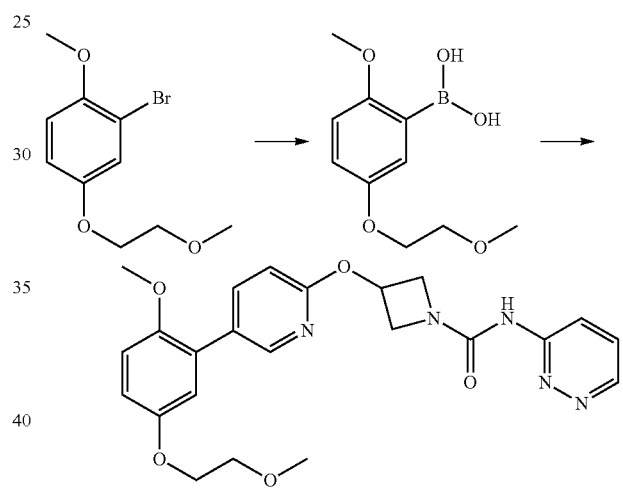

A solution of 2-bromo-1-methoxy-4-(2-methoxy-ethoxy)-benzene (110 mg, 0.42 mmol) in anhydrous THF (2 mL) was cooled to −78° C. with a $CO_2$— acetone bath under a nitrogen atmosphere. Triisopropyl borate (0.19 mL, 0.842 mmol) was added, followed by n-butyl lithium solution (2.5M in hexanes, 0.22 mL, 0.55 mmol). The mixture was allowed to warm to ambient temperature the solvents were removed in vacuo to afford a colourless solid. To the crude boronic acid was added 3-(5-iodo-pyridin-2-yloxy)-azetidine-1-carboxylic acid pyridazin-3-ylamide (Example 7, step 1) (150 mg, 0.38 mmol), 1N aqueous sodium bicarbonate solution (1.26 mL), DMF (7 mL) and 1,1'-bis[(diphenylphosphino)-ferrocene]dichloropalladium(10 complex with $CH_2Cl_2$ (15 mg). Nitrogen gas bubbled through mix for 5 minutes and reaction mixture heated at 80° C. for 2 hr. Mix was allowed to cool, partitioned between ethyl acetate (30 mL) and water (30 mL). Organic phase was separated then washed with sat. aqueous sodium chloride solution (60 mL) and dried over sodium sulphate. Solvents were removed in vacuo to afford a crude oil which was purified by flash chromatography on silica gel, eluting with a gradient of 0-10% ethyl acetate in hexane to afford the title compound (77 mg, 41%) as a pale yellow foam.

LCMS: (Method A) RT=1.94 min; m/z=450 [M−H]⁻ (negative ionisation).

TLC: $R_f$=0.21 (100% EtOAc)

¹H NMR: (400 MHz, CDCl₃) δ 3.45 (s, 3H), 3.75 (m, 2H), 3.77 (s, 3H), 4.12 (m, 2H), 4.21 (m, 2H), 4.56 (m, 2H), 5.48 (m, 1H), 6.83 (d, 1H, J=8.6 Hz), 6.91 (m, 3H), 7.42 (dd, 1H, J=9.1, 4.8 Hz), 7.47 (brs, 1H), 7.82 (dd, 1H, J=8.6, 2.5 Hz), 8.25 (d, 1H, J=2.3 Hz) 8.38 (dd, 1H, J=9.1, 1.3 Hz), 8.84 (dd, 1H, J=4.5, 1.3 Hz).

Example 12

3-[5-(2,5-Dimethoxy-phenyl)-pyridin-2-yloxy]-azetidine-1-carboxylic acid pyridazin-3-ylamide

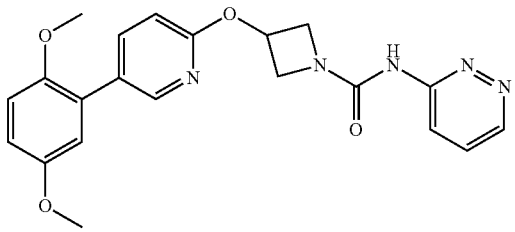 [SMILES: COc1ccc(OC)c(-c2ccc(OC3CN(C(=O)Nc4cccnn4)C3)nc2)c1]

This compound was prepared by the method outlined for example 5 step 6. Thus 3-(5-Iodo-pyridin-2-yloxy)-azetidine-1-carboxylic acid pyrazin-2-ylamide (100 mg, 0.25 mmol) was reacted with 2,5-Dimethoxybenzeneboronic acid (Cas. No 107099-99-0, 69 mg, 0.38 mmol) to afford title compound (84 mg, 83%) as an off-white powder.

LCMS: (Method B) RT=1.19 min; m/z=408 [M+H]⁺.

¹H NMR: (400 MHz, DMSO-d₆) δ 3.72 (s, 3H), 3.75 (s, 3H), 4.00-4.08 (m, 2H), 4.46-4.51 (m, 2H), 5.36-5.41 (m, 1H), 6.91-6.97 (m, 3H), 7.04-7.06 (m, 1H), 7.58 (dd, 1H, J=4.5, 9.1 Hz) 7.89 (dd, 1H, J=2.3, 8.6 Hz), 8.15 (dd, 1H, J=1.5, 9.1 Hz), 8.27 (d, 1H, J=1.7 Hz), 8.85 (dd, 1H, J=1.4, 4.6 Hz), 9.96 (s, 1H).

Example 13

3-(5-Phenyl-pyridin-2-yloxy)-azetidine-1-carboxylic acid pyridazin-3-ylamide

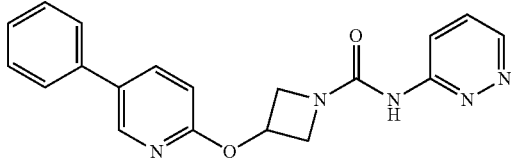 [SMILES: O=C(Nc1cccnn1)N1CC(Oc2ccc(-c3ccccc3)cn2)C1]

This compound was prepared by the method outlined for example 5 step 6. Thus 3-(5-Iodo-pyridiri-2-yloxy)-azetidine-1-carboxylic acid pyrazin-2-ylamide (750 mg, 1.89 mmol), benzeneboronic acid (345 mg, 2.83 mmol), potassium carbonate (783 mg, 5.67 mmol), [1,1'-bis(diphenylphosphino)ferrocene]dichloropalladium(II) (complex with dichloromethane; 155 mg, 0.19 mmol) and THF-H₂O (10:1; 0.15 mL) were mixed, sealed in two microwave vials and heated at 100° C. for 2 hours. The vials were combined, evaporated and loaded onto a 50 g SiO₂ cartridge in DCM, and dried thoroughly. The product was eluted with 1:1 iso-hexane:EtOAc to EtOAc and the product obtained after evaporation of the product-containing fractions triturated in 2:1 diethyl ether-iso-hexane and collected by filtration to give the product (702 mg, 54%) as a white powder; mp 201-202° C.; $R_f$ 0.17 (EtOAc); LCMS rt 1.19 mins [Method B], m/z 348 ([M+H]⁺, 100%); $□_H$ (399 MHz; DMSO-d₆) 9.97 (1H, br s), 8.85 (1H, dd, J=4.5 and 1.3 Hz), 8.48 (1H, dd, J=2.5 and 0.5 Hz), 8.15 (1H, dd, J=9.1 and 1.5 Hz), 8.08 (1H, dd, J=8.6, 2.5 Hz), 7.68-7.66 (2H, m), 7.59 (1H, dd, J=9.1 and 4.5 Hz), 7.49-7.45 (2H, m), 7.39-7.36 (1H, m), 7.01 (1H, dd, J=8.6 and 0.5 Hz), 5.40 (1H, tt, J=6.6 and 4.0 Hz), 4.48 (2H, dd, J=8.6 and 6.6 Hz) and 4.04 (2H, dd, J=9.6 and 3.0 Hz).

Example 14

3-[5-(2,6-Difluoro-phenyl)-pyridin-2-yloxy]-azetidine-1-carboxylic acid pyridazin-3-ylamide

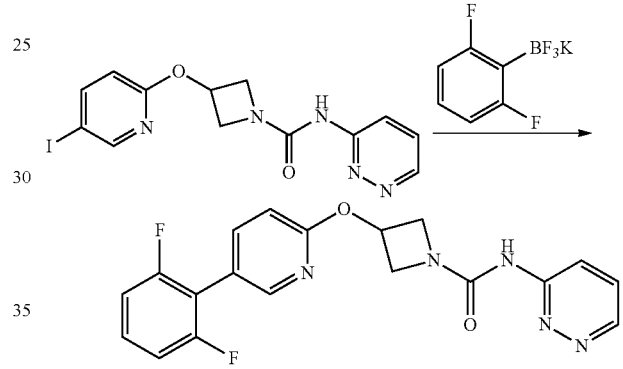

3-(5-iodo-pyridin-2-yloxy)-azetidine-1-carboxylic acid pyrimidin-4-ylamide (50 mg, 0.126 mmol), potassium 2,6-difluorophenyltrifluoroborate (29 mg, 0.132 mmol), triethylamine (0.05 ml, 0.38 mmol) 1,1'-bis[(diphenylphosphino)-ferrocene]dichloropalladium(II) complex with CH₂Cl₂ (5 mg, 5 mole %) and EtOH (108 mg, 0.786 mmol) were combined and heated at 80° C. for 16 h. The reaction had not gone to completion so further potassium 2,6-difluorophenyltrifluoroborate (29 mg, 0.132 mmol), 1,1'-bis[(diphenylphosphino)-ferrocene]dichloropalladium(II) complex with CH₂Cl₂ (5 mg, 5 mole %) and triethylamine (0.05 ml, 0.38 mmol) were added and the mixture heated for a further 5 h. The reaction mixture was allowed to cool before being passed through a pad of celite and washed through with EtOAc and MeOH. These organics were evaporated in vacuo, to afford a crude oil, which was purified by flash chromatography, eluting with a gradient of 0 to 4% MeOH in CH₂Cl₂ to a afford still impure product as a brown oil. This was purified by HPLC (pH 4, HCO₂NH₄/HCO₂H/H₂O/MeCN) to afford the desired product as a white solid (8 mg, 17%)

LCMS: (Method B) RT=1.2 min; m/z=384 [M+H]⁺

¹H NMR: (400 MHz, CDCl₃) δ 4.06 (m, 2H), 4.50 (m, 2H), 5.41 (m, 1H), 7.07 (m, 1H, J=8.6, 0.5 Hz), 7.26 (m, 2H), 7.51 (m, 1H), 7.59 (dd, 1H, J=4.5 Hz), 7.89 (m, 1H), 8.15 (dd, 1H, J=9.0, 1.5 Hz) 8.28 (m, 1H), 8.85 (dd, 1H, J=4.5, 1.3 Hz), 9.97 (bs, 1H).

Example 15

1-(3-{5-[2-Chloro-5-(2-methoxy-ethoxy)-phenyl]-pyridin-2-yloxy}-azetidin-1-yl)-2-pyridazin-3-yl-ethanone

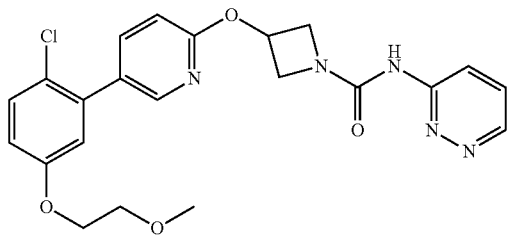 [SMILES: COCCOc1ccc(Cl)c(-c2ccc(OC3CN(C(=O)Nc4cccnn4)C3)nc2)c1]

Step 1

4-Chloro-3-(4,4,5,5-tetramethyl-[1,3,2]dioxaborolan-2-yl)-phenol

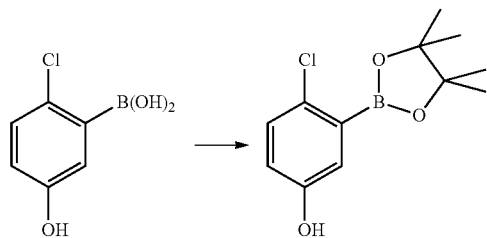 [SMILES: OB(O)c1cc(O)ccc1Cl ; CC1(C)OB(c2cc(O)ccc2Cl)OC1(C)C]

2-chloro-5-hydroxyphenyl boronic acid (409 mg, 2.37 mmol), pinacol (336 mg, 2.85 mmol), toluene (20 ml) and 4 angstrom molecular sieves (400 mg) were combined and heated at 120° C. for 2 h. The reaction mixture was allowed to cool and was then partitioned between EtOAc (2×30 ml) and water (30 ml). The combined organics were washed with brine (20 ml), dried (Na$_2$SO$_4$) and evaporated in vacuo to afford the desired product as a white solid (500 mg, 83%).

LCMS: (Method A) RT=2.35 min; m/z=253 [M−H]$^-$.

Step 2

1-(3-{5-[2-Chloro-5-(2-methoxy-ethoxy)-phenyl]-pyridin-2-yloxy}-azetidin-1-yl)-2-pyridazin-3-yl-ethanone

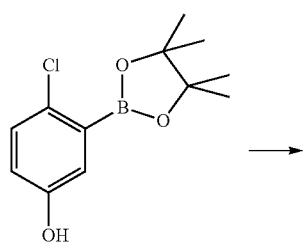

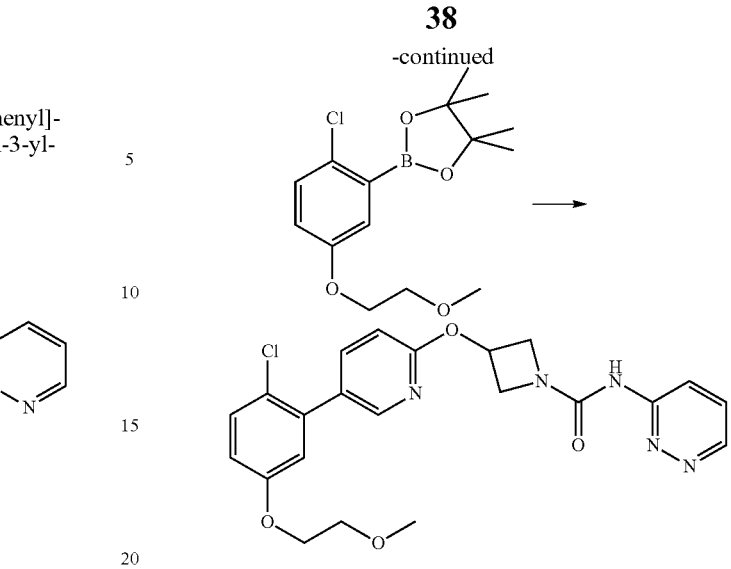

4-Chloro-3-(4,4,5,5-tetramethyl-[1,3,2]dioxaborolan-2-yl)-phenol (495 mg, 1.95 mmol), PPh$_3$ (765 mg, 2.92 mmol) and THF (11 ml) were combined under N$_2$ at RT. 2-methoxyethanol (0.18 ml, 2.34 mmol) was then added and the reaction mixture stirred for 5 min. The mixture was then cooled to 0° C. and DIAD (0.57 ml, 2.92 mmol) added dropwise. The mixture was then allowed to warm to RT and stirred for a further 2 h. The reaction mixture was partitioned between EtOAc (2×30 ml) and water (30 ml). The combined organics were washed with brine (30 ml), dried (Na$_2$SO$_4$) and evaporated in vacuo to afford the crude product as a yellow oil, which was purified by flash chromatography, eluting with a gradient of 0 to 50% EtOAc in Hexane to a afford still impure product as an off-white solid (316 mg, impure). This was combined with 3-(5-iodo-pyridin-2-yloxy)-azetidine-1-carboxylic acid pyrimidin-4-ylamide (64 mg, 0.162 mmol), 1M NaHCO$_3$ solution (0.19 ml, 0.194 mmol), PdCl$_2$(PPh$_3$)$_2$ (6 mg, 2 mol %) and DMF (4 ml). The mixture was degassed by bubbling N$_2$ through it for 5 min. and was subsequently heated at 80° C. for 2 h under N$_2$. The reaction was allowed to cool before being filtered through a pad of celite before being partitioned between EtOAc (2×20 ml) and water (25 ml). The combined organics were dried (Na$_2$SO$_4$) and evaporated in vacuo to give a crude oil, which was purified by flash chromatography, eluting with a gradient of 0 to 10% MeOH in CH$_2$Cl$_2$ to a afford still impure product as a brown oil. This was purified by HPLC (pH 4, HCO$_2$NH$_4$/HCO$_2$H/H$_2$O/MeCN) to afford the desired product as a white solid (48 mg, 26%)

LCMS: (Method B) RT=1.28 min; m/z=456 [M+H]$^+$
$^1$H NMR: (400 MHz, CDCl$_3$) δ 3.30 (s, 3H), 3.65 (m, 2H), 4.05 (m, 2H), 4.15 (m, 2H), 4.50 (m, 2H), 5.41 (m, 1H), 7.01 (m, 3H), 7.47 (d, 1H, J=8.8 Hz), 7.59 (dd, 1H, J=4.5 Hz), 7.89 (dd, 1H, J=8.6, 2.5 Hz), 8.15 (dd, 1H, J=9.1, 1.5 Hz) 8.25 (d, 1H, J=2.5 Hz), 8.85 (dd, 1H, J=4.5, 1.5 Hz), 9.97 (bs, 1H).

Example 16

3-[5-(2-Fluoro-phenyl)-pyridin-2-yloxy]-azetidine-1-carboxylic acid pyrazin-2-ylamide

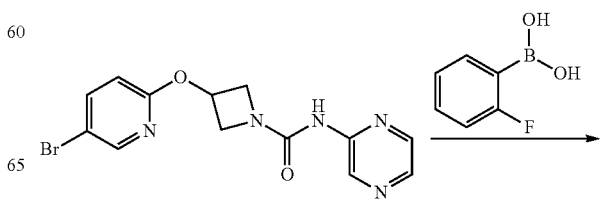

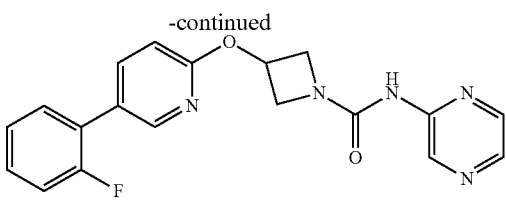

To a mixture of 3-(5-bromo-pyridin-2-yloxy)-azetidine-1-carboxylic acid pyrazin-2-ylamide (Example 6 step 4; 100 mg, 0.285 mmol), 2-fluorophenylboronic acid (Aldrich, 60 mg, 0.428 mmol), potassium carbonate (118 mg, 0.86 mmol) and 1,1'-bis[(diphenylphosphino)-ferrocene]dichloropalladium(II) complex with $CH_2Cl_2$ (23 mg, 10 mole %) in a microwave vial was added $THF/H_2O$ (10:1, 3 mL). Nitrogen gas was bubbled through the mixture for 5 mins and the vial sealed and heated at 100° C. in microwave synthesizer for 20 min. The cooled reaction mixture was diluted with ethyl acetate (20 mL) and filtered through celite (2.5 g IST cartridge). A further 10 mL of ethyl acetate was washed through the celite pad and combined filtrate was washed sequentially with water (25 mL) then sat. sodium chloride solution (25 mL). Mixture was dried over sodium sulphate and filtered. Filtrate solvents were removed in vacuo to afford a crude product, which was purified by flash chromatography, eluting with a gradient of 50 to 100% ethyl acetate in hexane to a afford a gummy solid. which was triturated with diethyl ether, filtered and dried to afford the title compound as colourless solid (67 mg, 64%)

LCMS: (Method A) RT=2.09 min; m/z=366.1 [M+H]$^+$.
TLC: $R_f$=0.16 (EtOAc/Hexane, 1:1)
$^1$H NMR: (400 MHz, DMSO-$d_6$) δ 4.00-4.07 (m, 2H), 4.44-4.57 (m, 2H), 5.37-5.43 (m, 1H), 7.03 (d, 1H, J=8.6 Hz), 7.29-7.37 (m, 2H), 7.40-7.48 (m, 1H), 7.54-7.60 (m, 1H), 7.95-7.99 (m, 1H), 8.22 (d, 1H, J=2.5 Hz), 8.29-8.31 (m, 1H), 8.34-8.36 (brm, 1H), 9.17 (d, 1H, J=1.6 Hz), 9.65 (s, 1H).

Example 17

3-[5-(2-Methoxy-phenyl)-pyridin-2-yloxy]-azetidine-1-carboxylic acid pyridazin-3-ylamine

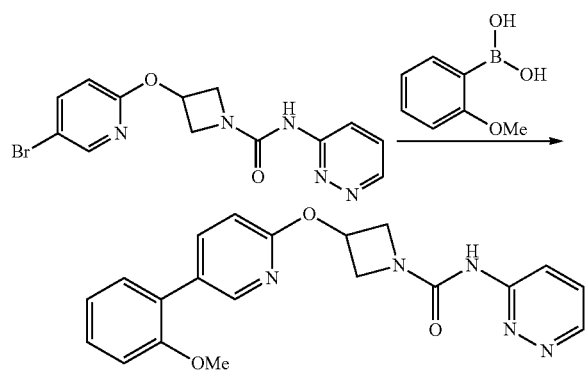

A solution of 2-methoxyphenyl boronic acid in $THF/H_2O$ (10:1; 40 mL) was added to a microwave vial containing 3-(5-bromo-pyridin-2-yloxy)-azetidine-1-carboxylic acid pyridazin-3-ylamide (prepared as in Example 19 Step 1) 1.5 g, 4.28 mmol) and potassium carbonate (1.78 g, 12.86 mmol). Nitrogen gas was bubbled through the mixture for 5 mins then 1,1'-bis[(diphenylphosphino)-ferrocene]dichloropalladium(II) complex with $CH_2Cl_2$ (0.350 g, 10 mole %) was added and the vial sealed and heated at 100° C. in microwave synthesiser for 30 min. The cooled reaction mixture was diluted with ethyl acetate (100 mL) and washed sequentially with sat. aqueous sodium carbonate solution (100 mL) then sat. sodium chloride solution (100 mL). Mixture dried over magnesium sulphate and filtered. Filtrate solvents were removed in vacuo to afford a brown gum, which was purified by flash chromatography, eluting with a gradient of 80 to 100% ethyl acetate in hexane to a afford a pale yellow solid. Product was triturated with diethyl ether, filtered and dried to afford the title compound as a white solid (1.098 g, 68%)

LCMS: (Method A) RT=2.04 min; m/z=378 [M+H]+.
$^1$H NMR: (400 MHz, DMSO-$d_6$) δ 3.78 (s, 3H), 4.04 (brm, 2H), 4.49 (brm, 2H), 5.39 (m, 1H), 6.96 (d, 1H, J=8.6 Hz), 7.04 (m, 1H), 7.13 (d, 1H, J=8.2 Hz), 7.33 (dd, 1H, J=7.5, 1.6 Hz), 7.37 (m, 1H), 7.59 (dd, 1H, J=9.1, 4.7 Hz), 7.88 (dd, 1H, J=8.6, 2.5 Hz), 8.16 (dd, 1H, J=9.1, 1.4 Hz), 8.25 (d, 1H, J=2.5 Hz), 8.85 (dd, 1H, J=4.7, 1.4 Hz), 9.96 (s, 1H).

Example 18

3-[5-(2-Fluoro-phenyl)-pyridin-2-yloxy]-azetidine-1-carboxylic acid pyridazin-3-ylamide

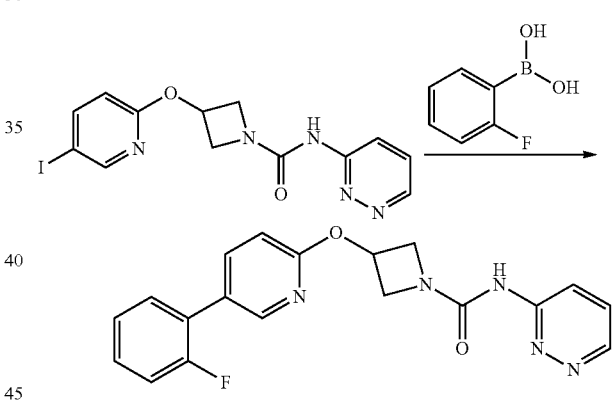

A solution of 4-fluorophenyl boronic acid (0.254 mg, 1.81 mmol) in $THF/H_2O$ (10:1; 10 mL) was added to a microwave vial containing 3-(5-iodo-pyridin-2-yloxy)-azetidine-1-carboxylic acid pyridazin-3-ylamide (Example 7, Step 1) (0.480 g, 1.21 mmol) and potassium carbonate (0.50 g, 3.63 mmol). Nitrogen gas was bubbled through the mixture for 5 mins then 1,1'-bis[(diphenylphosphino)-ferrocene]dichloropalladium(II) complex with $CH_2Cl_2$ (0.099 g, 10 mole %) was added and the vial sealed and heated at 100° C. in microwave synthesiser for 30 min. The cooled reaction mixture was diluted with ethyl acetate (20 mL) and washed sequentially with saturated aqueous sodium carbonate solution (20 mL) then saturated sodium chloride solution (20 mL). The mixture was dried over magnesium sulphate and filtered. Filtrate solvents were removed in vacuo to afford a brown gum, which was purified by flash chromatography, eluting with a gradient of 50% to 100% ethyl acetate in hexane to a afford a white solid (0.235 g, 53%)

LCMS: (Method B) RT=1.20 min; m/z=366 [M+H]$^+$.
$^1$H NMR: (400 MHz, DMSO-$d_6$) δ 4.05 (brm, 2H), 4.50 (brm, 2H), 5.41 (m, 1H), 7.04 (d, 1H, J=8.6 Hz), 7.29-7.38

(m, 2H), 7.45 (m, 1H), 7.54-7.62 (m, 2H), 7.97 (m, 1H), 8.15 (dd, 1H, J=9.1, 1.4 Hz), 8.36 (app s, 1H), 8.85 (dd, 1H, J=4.6, 1.4 Hz), 9.97 (s, 1H).

Example 19

3-[5-(2-Fluoro-3-methoxy-phenyl)-pyridin-2-yloxy]-azetidine-1-carboxylic acid pyridazin-3-ylamide

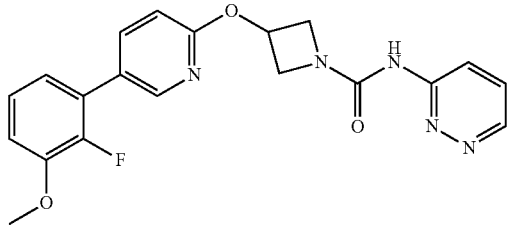 [SMILES: COc1cccc(-c2ccc(OC3CN(C(=O)Nc4cccnn4)C3)nc2)c1F]

Step 1

Synthesis of 3-(5-Bromo-pyridin-2-yloxy)-azetidine-1-carboxylic acid pyridazin-3-ylamide

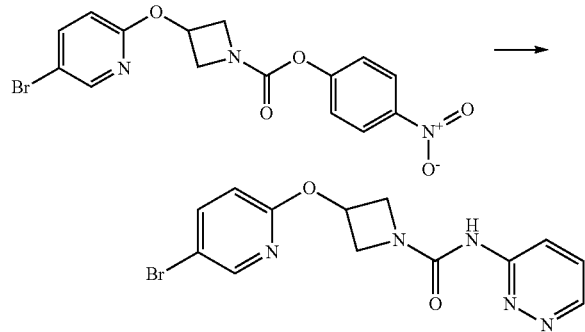

To an ice-bath cooled solution of sodium hydride (60 wt % in mineral oil, (0.946 g, 23.6 mmol) in DMF (21 mL) under nitrogen atmosphere was added (dropwise) a solution of 3-aminopyridazine (1.24 g, 13.01 mmol) in DMF (21 mL). After several minute a solution of 3-(5-bromo-pyridin-2-yloxy)-azetidine-1-carboxylic acid 4-nitro-phenyl ester (Example 10, step 3; 4.66 g, 11.83 mmol) in DMF (17 mL) was added. After 5 min the cooling bath was removed and reaction allowed to warm to ambient temperature and stir for 1.5 hr. Saturated sodium bicarbonate solution (500 mL) was added and the mixture was extracted with EtOAc (4×400 mL). Combined organic phases were washed with sat sodium chloride solution (500 mL), dried over sodium sulphate and filtered. The filtrate solvents were removed in vacuo to afford a crude product that was triturated with diethyl ether to afford the title compound (3.32 g, 80%) as a colourless solid.

LCMS: (Method A) RT=1.81 min; m/z=352 [M+H]$^+$.

Step 2

3-[5-(2-Fluoro-3-methoxy-phenyl)-pyridin-2-yloxy]-azetidine-1-carboxylic acid pyridazin-3-ylamide

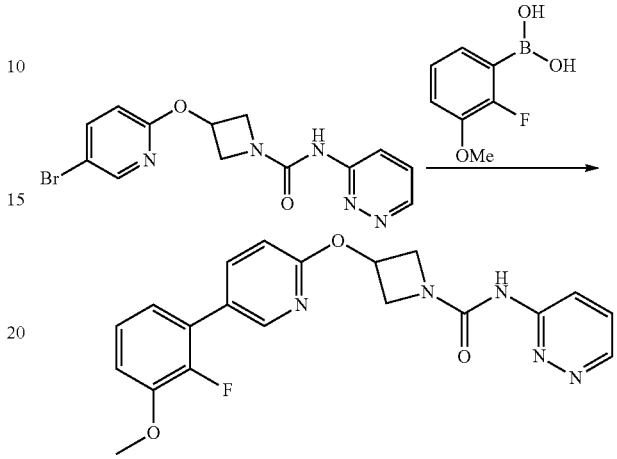

A solution of 2-fluoro-3-methoxyphenyl boronic acid (0.065 g, 0.38 mmol) in THF/H$_2$O (10:1; 2 mL) was added to a microwave vial containing 3-(5-bromo-pyridin-2-yloxy)-azetidine-1-carboxylic acid pyridazin-3-ylamide (prepared in Step 1) (0.100 g, 0.25 mmol) and potassium carbonate (0.105 g, 0.76 mmol). Nitrogen gas was bubbled through the mixture for 5 mins then 1,1'-bis[(diphenylphosphino)-ferrocene]dichloropalladium(II) complex with CH$_2$Cl$_2$ (0.020 g, 10 mole %) was added and the vial sealed and heated at 100° C. in microwave synthesiser for 30 min. The cooled reaction mixture was diluted with ethyl acetate (20 mL) and washed sequentially with sat. aqueous sodium carbonate solution (20 mL) then sat. sodium chloride solution (20 mL). Mixture dried over magnesium sulphate and filtered. Filtrate solvents were removed in vacuo to afford a brown gum, which was purified by flash chromatography, eluting with a gradient of 80 to 100% ethyl acetate in hexane to a afford an off-white solid (0.079 g, 78%).

LCMS: (Method B) RT=1.18 min; m/z=408 [M+H]$^+$.

$^1$H NMR: (400 MHz, DMSO-d$_6$) δ 3.88 (s, 3H), 4.05 (brm, 2H), 4.49 (brm, 2H), 5.41 (m, 1H), 7.03 (d, 1H, J=8.6 Hz), 7.08 (m, 1H), 7.17-7.26 (m, 2H), 7.59 (dd, 1H, J=9.1, 4.6 Hz), 7.94 (m, 1H), 8.15 (dd, 1H, J=9.1, 1.4 Hz), 8.33 (app s, 1H), 8.85 (dd, 1H, J=4.6, 1.4 Hz), 9.96 (s, 1H).

Example 20

3-[5-(2-Fluoro-phenyl)-pyridin-2-yloxy]-azetidine-1-carboxylic acid (6-methyl-pyridazin-3-yl)-amide

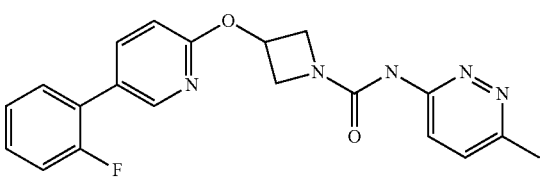 [SMILES: Cc1ccc(NC(=O)N2CC(Oc3ccc(-c4ccccc4F)cn3)C2)nn1]

Step 1

2-(1-Benzhydryl-azetidin-3-yloxy)-5-(2-fluoro-phenyl)-pyridine

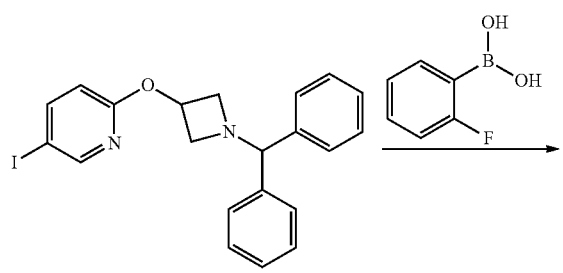

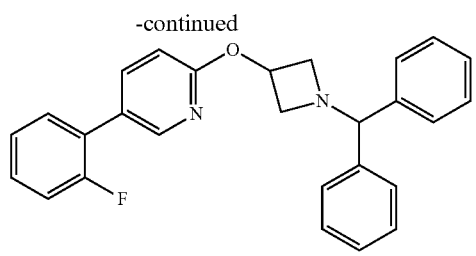

To a solution of 2-fluoro-boronic acid (1.45 g, 10.36 mmol) and 2-(1-Benzhydryl-azetidin-3-yloxy)-5-iodo-pyridine (3.53 g, 7.97 mmol) in DMF (180 mL) was added sodium hydrogen carbonate (2.01 g) suspended in water (20 mL). The reaction mixture was stirred under a flow of nitrogen for 1 hr. then 1,1-bis[(diphenylphosphino)-ferrocene]dichloropalladium(II) complex with $CH_2Cl_2$ (326 mg, 5 mole %) was added and stirred for 18 hrs at room temperature.

The reaction mixture was concentrated in vacuo, diluted with ethyl acetate (400 mL) filtered over Celite and washed sequentially with sat. aqueous sodium hydrogen carbonate solution (3×150 mL) then sat. sodium chloride solution (150 mL). Mixture dried over magnesium sulphate and filtered. Filtrate solvents were removed in vacuo and the residue was purified by flash chromatography (4% Methanol in DCM) to give the title compound (2.18 g, 67%)

LCMS: (Method A) RT=2.54 min; m/z=411 [M+H]$^+$.

$^1$H NMR: (400 MHz, CDCl$_3$) δ 3.12-3.20 (m, 2H), 3.74-3.80 (m, 2H), 4.45 (s, 1H), 5.27-5.33 (m, 1H), 6.81 (d, 1H, J 8.6), 7.11-7.22 (m, 4H), 7.28-7.40 (m, 6H), 7.43-7.46 (m, 4H), 7.75-7.78 (m, 1H), 8.21-8.28 (m, 1H).

Step 2

3-[5-(2-Fluoro-phenyl)-pyridin-2-yloxy]-azetidine-1-carboxylic acid 4-nitro-phenyl ester

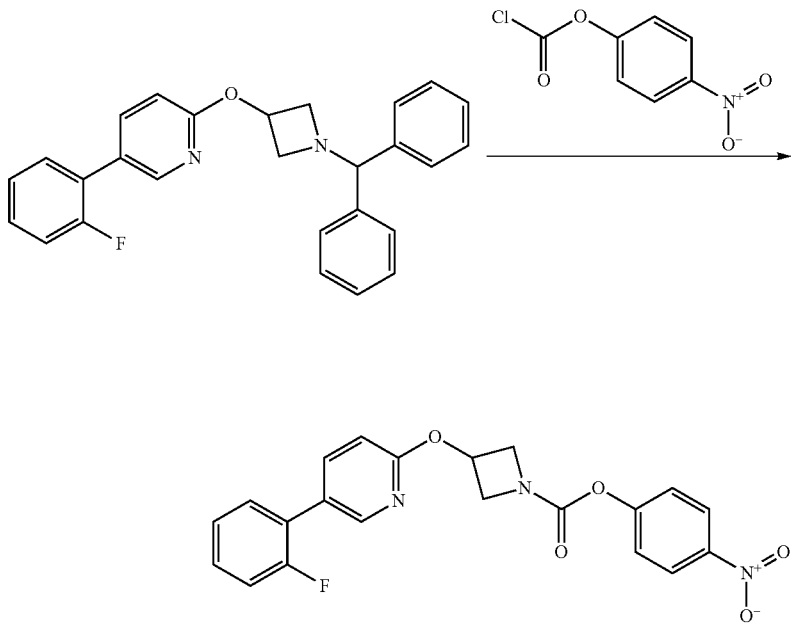

4-nitrophenyl chloroformate (734 mg g, 3.64 mmol) was added to a stirred solution of 2-(1-Benzhydryl-azetidin-3-yloxy)-5-(2-fluoro-phenyl)-pyridine (996 mg, 2.43 mol) in dichloromethane (25 mL) at ambient temperature. The resulting solution was stirred at ambient temperature for 18 hr, diluted with dichloromethane (150 mL) and washed sequentially with sat. aqueous sodium hydrogen carbonate solution (3×150 mL) then sat. sodium chloride solution (150 mL). The organic phase was dried over magnesium sulphate and filtered. Filtrate solvents were removed in vacuo and the residue was purified by trituration with Methyl tertiary butyl ether (25 mL) to give after filtration a yellow solid (786 mg, 79%).

LCMS: (Method A) RT=2.46 min; m/z=410 [M+H]$^+$.

$^1$H NMR: (400 MHz, CDCl$_3$) δ 4.20-4.26 (m, 1H), 4.26-4.34 (m, 1H), 4.52-4.60 (m, 1H), 4.60-4.72 (m, 1H), 5.46-5.52 (m, 1H), 6.90 (d, 1H, J 8.6), 7.15-7.25 (m, 2H), 7.33 (d, 2H, J 9.4), 7.31-7.43 (m, 3H), 7.82-7.86 (m, 1H), 8.25 (d, 2H, J 9.1), 8.28-8.32 (m, 1H).

Step 3

3-[5-(2-Fluoro-phenyl)-pyridin-2-yloxy]-azetidine-1-carboxylic acid (6-methyl-pyridazin-3-yl)-amide

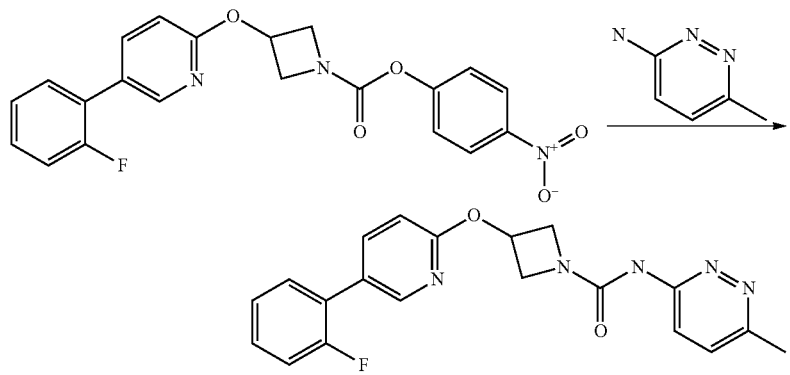

To a solution of 6-Methyl-pyridazin-3-ylamine (60 mg, 0.55 mmol, [Cas. No 18591-82-7]) in DMF (3 mL) at 0° C. was added sodium hydride (20 mg, 0.5 mmol, 60% disp. in mineral oil). After stirring at 0° C. for 15 min. a solution of 3-[5-(2-Fluoro-phenyl)-pyridin-2-yloxy]-azetidine-1-carboxylic acid 4-nitro-phenyl ester (102 mg, 0.25 mmol) in DMF (4 mL) was added dropwise. After stirring for 16 hrs at ambient temperature the reaction mixture was concentrated in vacuo, diluted with ethyl acetate (50 mL) and washed sequentially with sat. aqueous sodium hydrogen carbonate solution (2×50 mL) then sat. sodium chloride solution (50 mL). Mixture dried over magnesium sulphate and filtered. Filtrate solvents were removed in vacuo and the residue was purified by flash chromatography (40% ethyl acetate in DCM) to give the title compound (48 mg, 49%) LCMS: (Method A) RT=1.86 min; m/z=380 [M+H]$^+$.

$^1$H NMR: (400 MHz, CDCl$_3$) δ 2.60 (s, 3H), 4.19-4.23 (m, 2H), 4.54-4.58 (m, 2H), 5.45-5.50 (m, 1H), 6.88 (d, 1H, J 8.6), 7.14-7.24 (m, 2H), 7.27-7.41 (m, 3H), 7.80-7.84 (m, 1H), 8.25-8.30 (m, 2H).

Example 21

3-[5-(2-Fluoro-phenyl)-pyridin-2-yloxy]-azetidine-1-carboxylic acid (6-methoxy-pyridazin-3-yl)-amide

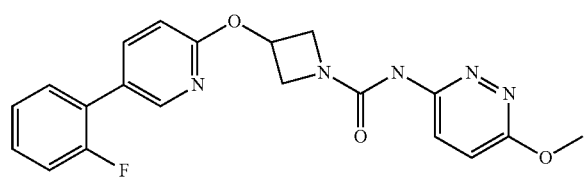 [SMILES: COc1ccc(NC(=O)N2CC(Oc3ccc(-c4ccccc4F)cn3)C2)nn1]

To a solution of 6-Methoxy-pyridazin-3-ylamine (39 mg, 0.31 mmol, [Cas. No. 7252-84-8]) in DMF (3 mL) at 0° C. was added sodium hydride (20 mg, 0.5 mmol, 60% disp. in mineral oil). After stirring at 0° C. for 15 min. a solution of 3-[5-(2-Fluoro-phenyl)-pyridin-2-yloxy]-azetidine-1-carboxylic acid 4-nitro-phenyl ester (102 mg, 0.25 mmol) in DMF (4 mL) was added dropwise. After stirring for 16 hrs at ambient temperature the reaction mixture was concentrated in vacuo, diluted with ethyl acetate (50 mL) and washed sequentially with sat. aqueous sodium hydrogen carbonate solution (2×50 mL) then sat. sodium chloride solution (50 mL). Mixture dried over magnesium sulphate and filtered. Filtrate solvents were removed in vacuo and the residue was purified by flash chromatography (ethyl acetate) to give the title compound (35 mg, 37%)

LCMS: (Method A) RT=1.97 min; m/z=396 [M+H]$^+$.

$^1$H NMR: (400 MHz, CDCl$_3$) δ 4.03 (s, 3H), 4.21-4.25 (m, 2H), 4.55-4.59 (m, 2H), 5.45-5.50 (m, 1H), 6.88 (d, 1H, J 8.6), 7.02 (d, 1H, J 9.6), 7.15-7.25 (m, 2H), 7.31-7.42 (m, 2H), 7.81-7.84 (m, 1H), 8.28 (bs, 1H), 8.35 (d, 1H, J 9.3).

Example 22

3-[5-(2-Fluoro-phenyl)-pyridin-2-yloxy]-azetidine-1-carboxylic acid (5-methyl-[1,3,4]oxadiazol-2-yl)-amide

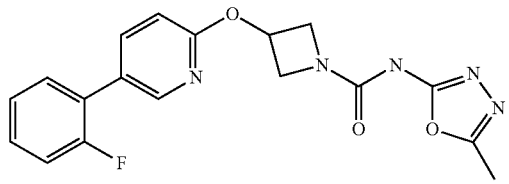 [SMILES: Cc1nnc(NC(=O)N2CC(Oc3ccc(-c4ccccc4F)cn3)C2)o1]

To a solution of 5-Methyl-[1,3,4]oxadiazol-2-ylamine (31 mg, 0.31 mmol, [Cas. No. 52838-39-8]) in DMF (3 mL) at 0° C. was added sodium hydride (20 mg, 0.5 mmol, 60% disp. in mineral oil). After stirring at 0° C. for 15 min. a solution of 3-[5-(2-Fluoro-phenyl)-pyridin-2-yloxy]-azetidine-1-carboxylic acid 4-nitro-phenyl ester (102 mg, 0.25 mmol) in DMF (4 mL) was added dropwise. After stirring for 16 hrs at ambient temperature the reaction mixture was concentrated in vacuo, diluted with ethyl acetate (50 mL) and washed sequentially with sat. aqueous sodium hydrogen carbonate solution (2×50 mL) then sat. sodium chloride solution (50 mL). Mixture dried over magnesium sulphate and filtered. Filtrate solvents were removed in vacuo and the residue was purified by preparative HPLC to give the title compound (10 mg, 11%) LCMS: (Method A) RT=1.77 min; m/z=370 [M+H]$^+$.

$^1$H NMR: (400 MHz, CD$_3$OD) δ 2.34 (s, 3H), 3.96-4.00 (m, 2H), 4.36-4.40 (m, 2H), 5.33-5.39 (m, 1H), 6.94 (d, 1H, J 8.8), 7.18-7.29 (m, 2H), 7.36-7.41 (m, 1H), 7.46-7.50 (m, 1H), 7.88-7.91 (m, 1H), 8.29 (bs, 1H).

Example 23

3-[5-(2-Fluoro-phenyl)-pyridin-2-yloxy]-azetidine-1-carboxylic acid pyridazin-4-ylamide

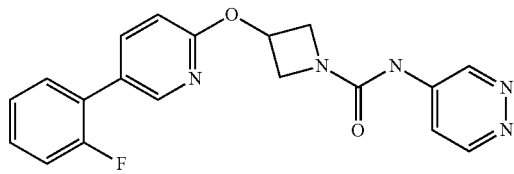 [SMILES: O=C(Nc1ccnnc1)N1CC(Oc2ccc(-c3ccccc3F)cn2)C1]

To a solution of Pyridazin-4-ylamine (30 mg, 0.31 mmol, [Cas. No. 20744-39-2]) in DMF (3 mL) at 0° C. was added sodium hydride (20 mg, 0.5 mmol, 60% disp. in mineral oil). After stirring at 0° C. for 15 min. a solution of 3-[5-(2-Fluoro-phenyl)-pyridin-2-yloxy]-azetidine-1-carboxylic acid 4-nitro-phenyl ester (102 mg, 0.25 mmol) in DMF (4 mL) was added dropwise. After stirring for 16 hrs at ambient temperature the reaction mixture was concentrated in vacuo, diluted with ethyl acetate (50 mL) and washed sequentially with sat. aqueous sodium hydrogen carbonate solution (2×50 mL) then sat. sodium chloride solution (50 mL). Mixture dried over magnesium sulphate and filtered. Filtrate solvents were removed in vacuo and the residue was purified by preparative HPLC to give the title compound (15 mg, 16%)

LCMS: (Method A) RT=1.74 min; m/z=366 [M+H]$^+$.

$^1$H NMR: (400 MHz, CD$_3$OD) δ 4.15-4.18 (m, 2H), 4.56-4.61 (m, 2H), 5.46-5.51 (m, 1H), 6.98 (d, 1H, J 8.6), 7.19-7.29 (m, 2H), 7.37-7.42 (m, 1H), 7.46-7.50 (m, 1H), 7.91-7.94 (m, 1H), 7.95-7.98 (m, 1H), 8.31 (bs, 1H), 8.87 (d, 1H, J 6.1), 9.26-9.28 (m, 1H).

Example 24

6-Chloro-4-methyl-pyridazin-3-ylamine and 6-Chloro-5-methyl-pyridazin-3-ylamine

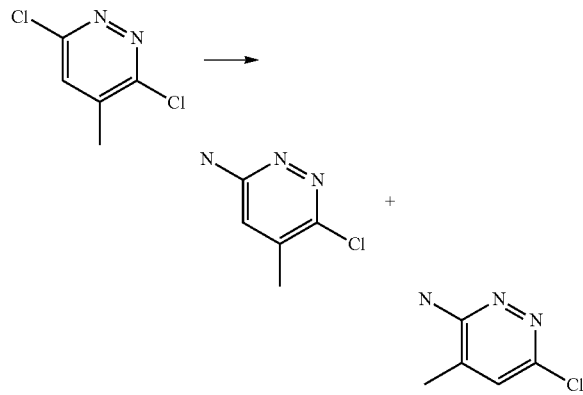

A solution of 3,6-Dichloro-4-methyl-pyridazine (3.0 g, 18.40 mmol) in Ammonia (28-30%; 150 mL) was heated at 130° C. in a pressurised reaction vessel for 16 hrs. The reaction mixture was cooled to ambient temperature and extracted with dichloromethane (10×100 mL) The organic layers were combined, dried (MgSO$_4$), filtered and concentrated to give a mixture of the titled compounds (853 mg; 32%).

LCMS: (Method A) RT=0.45 min; m/z=144 [M+H]$^+$.

$^1$H NMR: (400 MHz, DMSO-d$_6$) δ 2.07 (s, 3H), 2.18 (s, 3H), 6.47 (bs, 2H), 6.49 (bs, 2H), 6.74 (s, 1H), 7.31 (s, 1H).

Example 25

3-[5-(2-Fluoro-phenyl)-pyridin-2-yloxy]-azetidine-1-carboxylic acid (5-methyl-pyridazin-3-yl)-amide and 3-[5-(2-Fluoro-phenyl)-pyridin-2-yloxy]-azetidine-1-carboxylic acid (4-methyl-pyridazin-3-yl)-amide

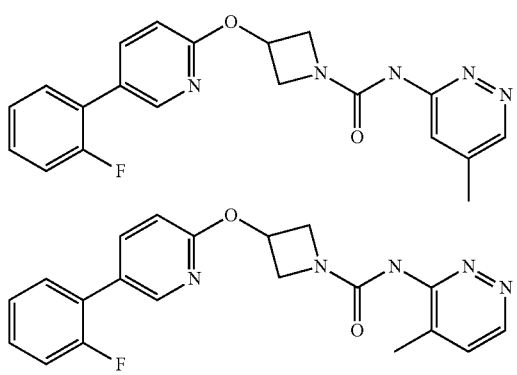

To a solution of the mixture 6-Chloro-4-methyl-pyridazin-3-ylamine and 6-Chloro-5-methyl-pyridazin-3-ylamine (143 mg, 1.0 mmol) in DMF (6 mL) at 0° C. was added sodium hydride (80 mg, 2.0 mmol, 60% disp. in mineral oil). After stirring at 0° C. for 15 min. a solution of 3-[5-(2-Fluoro-phenyl)-pyridin-2-yloxy]-azetidine-1-carboxylic acid 4-nitro-phenyl ester (204 mg, 0.5 mmol) in DMF (6 mL) was added dropwise. After stirring for 16 hrs at ambient temperature the reaction mixture was concentrated in vacuo, diluted with ethyl acetate (50 mL) and washed sequentially with sat. aqueous sodium hydrogen carbonate solution (2×50 mL) then sat. sodium chloride solution (50 mL). Mixture dried over magnesium sulphate and filtered. Filtrate solvents were removed in vacuo and the regioisomers were partially separated by flash chromatography (4% Methanol in DCM) which were separately hydrogenated at atmospheric pressure (10% Pd/C, Ethanol) to give after preparative HPLC purification the regioisomers.

3-[5-(2-Fluoro-phenyl)-pyridin-2-yloxy]-azetidine-1-carboxylic acid (5-methyl-pyridazin-3-yl)-amide (24 mg, 6%).

LCMS: (Method A) RT=1.91 min; m/z=380 [M+H]$^+$.

$^1$H NMR: (400 MHz, CD$_3$OD) δ 2.38 (s, 3H), 4.15-4.18 (m, 2H), 4.56-4.61 (m, 2H), 5.45-5.51 (m, 1H), 6.98 (d, 1H, J 8.6), 7.19-7.29 (m, 2H), 7.37-7.41 (m, 1H), 7.46-7.50 (m, 1H), 7.90-7.93 (m, 1H), 8.12 (bs, 1H), 8.31 (bs, 1H), 8.69 (bs, 1H).

3-[5-(2-Fluoro-phenyl)-pyridin-2-yloxy]-azetidine-1-carboxylic acid (4methyl-pyridazin-3-yl)-amide (11 mg, 3%)

LCMS: (Method A) RT=1.82 min; m/z=380 [M+H]$^+$.

Biological Results

Part A

Rat FAAH Inhibition Assay

Active rat FAAH protein (30-579) was isolated as described in the literature. The coding sequence of amino acids 30-579 of rat FAAH were cloned into the expression vector pET28a to provide an N-terminal His-tag. Following expression, the His-tagged FAAH (30-579) was isolated using a method based on Patricelli et al., 1998; Biochemistry vol 37, p 15177 with a combination of chelating sepharose, heparin sepharose and size exclusion chromatography.

FAAH activity was determined by measuring the liberation of the highly fluorescent 7-amino, 4-methyl Coumarin (AMC) generated during hydrolysis of the substrate Arachidonoyl 7-Amino, 4-methyl Coumarin Amide (AAMCA) by FAAH. Inhibition of FAAH activity was determined as a percentage reduction of the fluorescence determined in the absence of compound.

The assay was carried out in black-walled, clear bottom, 384-well plates. 27.5 µl of FAAH protein (in FAAH assay buffer: 50 mM Hepes, 0.01% Triton X-100, 1 mM EDTA, 0.5 mg/ml BSA (fatty-acid-free), pH 8.2) was pre-incubated, at 120 nM, with increasing concentrations of compounds (2.5 µl in 100% DMSO) for 0, 1 or 3 hours at room temperature. 2.5 µl of DMSO was added for 'total' controls (100% FAAH activity) and 2.5 µl of URB-597, a known inhibitor of FAAH activity, (at a final, saturating, concentration of 10 µM) was used for 'non-specific' controls (0% FAAH activity). 20 µl of 7.5 µM AAMCA substrate (in FAAH assay buffer) was then added to all wells and incubated at room temperature for a further 1.5 hours. Fluorescence was determined at an excitation wavelength of 355 nm and an emission wavelength of 460 nm using a Flexstation plate reader (Molecular Devices, UK). Inhibition of FAAH activity, by the compounds, was determined as the percentage reduction in relative fluorescence units (RFU) compared to the 'total' controls (in the absence of compound) minus the 'non-specific' controls. $IC_{50}$ values were determined, from 10-point dose response curves, in XL-Fit using a 4-Parameter Logistic Model (Sigmoidal Dose-Response Model).

The following Table 1 provides the 3-hour incubation results of testing the compounds of Examples 1-4 herein in the above rat FAAH inhibition assay.

TABLE 1

| Example No | FAAH Rat IC50 (nM) 180 minutes | n |
|---|---|---|
| 2 | 279 | 6 |
| 1 | 135 | 11 |
| 3 | 77 | 2 |
| 4 | 67 | 4 |

Part B
Human FAAH 1 Assay

Human FAAH 1 activity was determined by measuring the liberation of the highly fluorescent 7-amino, 4-methyl Coumarin (AMC) generated during hydrolysis of the substrate arachidonoyl 7-amino, 4-methyl coumarin amide (AAMCA) by FAAH. Inhibition of human FAAH 1 activity was determined as a percentage reduction of the fluorescence determined in the absence of compound.

The assay was carried out in black-walled, clear bottom, 384-well plates. 27.5 µl of human FAAH 1 protein (in FAAH assay buffer: 50 mM Hepes, 0.01% Triton X-100, 1 mM EDTA, 0.5 mg/ml BSA (fatty-acid-free), pH 8.2) was pre-incubated, at 10 nM, with increasing concentrations of compounds (2.5 µl in 100% DMSO) for 1 hour at room temperature. 2.5 µl of DMSO was added for 'total' controls (100% FAAH activity) and 2.5 µl of URB-597, a known inhibitor of FAAH activity, (at a final, saturating, concentration of 10 µM) was used for 'non-specific' controls (0 FAAH activity). 20 µl of 7.5 µM AAMCA substrate (in FAAH assay buffer) was then added to all wells and incubated at room temperature for a further 4 hours. Fluorescence was determined at an excitation wavelength of 355 nm and an emission wavelength of 460 nm using a Flexstation plate reader (Molecular Devices, UK). Inhibition of human FAAH 1 activity, by the compounds, was determined as the percentage reduction in relative fluorescence units (RFU) compared to the 'total' controls (in the absence of compound) minus the 'non-specific' controls. $IC_{50}$ values were determined, from 10-point dose response curves, in XL-Fit using a 4-Parameter Logistic Model (Sigmoidal Dose-Response Model).

Table 2 shows the 1 hour incubation results of testing the compounds of Examples 5 to 19 herein in the above human FAAH inhibition assay.

TABLE 2

| Example No | FAAH Human IC50 (nM) 60 minutes (n = 2) |
|---|---|
| 5 | 9 |
| 6 | 73 |
| 7 | 19 |
| 8 | 18 |
| 9 | 3 |
| 10 | 49 |
| 11 | 19 |
| 12 | 12 |
| 13 | 38 |
| 14 | 14 |
| 15 | 7 |
| 16 | 42 |
| 17 | 12 |
| 18 | 16 |
| 19 | 26 |

Part C
Rat Carrageenan Induced Thermal Hyperalgesia Model of Inflammatory Pain.

Male Wistar rats were assessed for thermal pain sensitivity by applying a focused light beam onto the hind paws and recording the time to paw withdrawal, before and after local intraplantar administration of carrageenan. After 3 h, thermal pain sensitivity was reassessed in treated and untreated hind paws prior to dosing with test compound or vehicle. Indomethacin was administered as a positive control.

Procedure

Male Sprague Dawley rats were tail-marked, and acclimatised to the plantar boxes on 3 separate occasions (6, 5 and 1 day prior to the test day) for at least 5 min on each occasion. On the pre-test day, the rats were habituated to the test room for at least 30 min prior to testing. The rats were put into the Hargreaves plantar boxes, allowed to settle down for approx 3-5 min, and challenged with the mobile radiant heat source. The latency to withdraw both left and right hindpaws from the heat source was determined on 2 occasions (3 min apart). The mean across the 2 challenges was recorded as the baseline for each animal. Rats 18 and 30 were not used in the study as they had very, high baseline readings, and they were replaced by 61 and 63. Rats were then allocated to drug treatments ensuring the baseline latencies were balanced across groups.

On the test day, rats received intraplantar carrageenan lambda (100 uL of 1% in saline), or saline in right hindpaw 3 hours before testing. Four hours before testing, rats received. VER-158416 (1, 3, or 10 mg/kg) or vehicle (5% EtOH: 95% (1% methylcellulose in water) p.o. Subsequently, 30 min before testing, rats received a second injection of either indomethacin 10 mg/kg or vehicle (50% 0.1M $Na_2CO_3$: 47.5% phosphate buffered saline (PBS): 2.5% 1M HCl) i.p. At the scheduled test time following drug treatment, the latency to withdraw the paw from the radiant heat source was reassessed by a single reading.

For example, the compound of Example 13 above was tested as follows:

Rats were dosed with intraplantar carrageenan at t=0; the compound of Example 13 (1, 3 & 10 mg/kg po) or vehicle (5% EtOH: 95% (1% methylcellulose in water) at t=2 h; indomethacin (10 mg/kg ip) or vehicle at t=2.5 h and thermal sensitivity was measured at t=3 h. Thus all rats received both oral and ip dosing.

The compound of Example 13 (1, 3, 10 mg/kg p.o.) caused a dose-related inhibition of carrageenan-induced thermal hypersensitivity, which reached statistical significance (cf. vehicle/carrageenan group; one way ANOVA followed by Newman-Keuls post hoc tests) at 3 and 10 mg/kg doses. The compound did not reduce pain sensitivity to below normal levels, and had no effect on contralateral paw sensitivities to thermal pain. The maximum effect of the compound was similar to that of the positive control indomethacin.

REFERENCES

Hargreaves, K., Dubner, R., Brown, F., Flores, C., Joris, J., (1988). A new and sensitive method for measuring thermal nociception in cutaneous hyperalgesia. Pain, 32, 77-88.

Hedo, G., Laird, J. M. A., Lopez-Garcia, J. A., (1999). Time course of spinal sensitization following carrageenan-induced inflammation in the young rat: a comparative electrophysiological and behavioural study in vitro and in vivo. Neuroscience, 92, 309-318

Morris, C. J., (2003). Carrageenan-induced paw edema in the rat and mouse. Methods in Mol Biol., 225, 115-121.

The invention claimed is:

1. A method of treatment of a disease or medical condition which benefits from inhibition of FAAH activity, wherein the disease or condition is selected from vomiting, nausea, depression, anxiety, spinal cord injury, and schizophrenia, comprising administering to a subject suffering such disease or condition an effective amount of a compound of formula (I), or a pharmaceutically acceptable salt thereof:

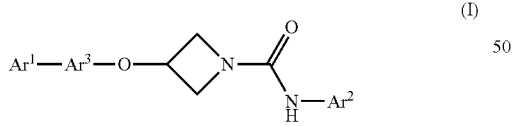

wherein
$Ar^1$ is optionally substituted phenyl or optionally substituted monocyclic heteroaryl having 5 or 6 ring atoms;
$Ar^2$ is optionally substituted phenyl, optionally substituted monocyclic heteroaryl having 5 or 6 ring atoms or optionally substituted fused bicyclic heteroaryl having 5 or 6 ring atoms in each fused ring; and
$Ar^3$ is a divalent radical selected from the group consisting of optionally substituted phenylene and optionally substituted monocyclic heteroarylene radicals having 5 or 6 ring atoms.

2. The method as claimed in claim 1 wherein $Ar^1$ is optionally substituted phenyl.

3. The method as claimed in claim 1 wherein $Ar^2$ is phenyl, pyridyl, pyrimidinyl, pyrazinyl or pyridazinyl, any of which being optionally substituted.

4. The method as claimed in claim 1 wherein $Ar^2$ is 3-pyridyl, pyrimidin-4-yl, pyrazin-2-yl or pyridazin-3-yl, any of which being optionally substituted.

5. The method as claimed in claim 1 wherein $Ar^3$ is an optionally substituted divalent phenylene or pyridinylene radical.

6. The method as claimed in claim 5 wherein $Ar^3$ is an optionally substituted divalent 1,4-phenylene or a 2,5-pyridinylene radical of formula:

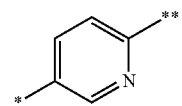

wherein the bond marked with a single asterisk is attached to $Ar^1$ and the bond marked with a double asterisk is attached to the oxygen.

7. The method as claimed in claim 1 wherein any optional substituents in $Ar^1$, $Ar^2$ and $Ar^3$ are independently selected from chloro, fluoro, bromo, cyclopropyl, methyl, mono-, di- or tri-methyl, trifluoromethyl, difluoromethyl, monofluoromethyl, methoxy, ethoxy, propoxy, butoxy, pentoxy, 2-methoxyethoxy, 2-benzyloxy-ethoxy, 2-hydroxy-ethoxy, mono-, di- or tri-fluoromethoxy, cyano, hydroxyl; —$CO_2R_1$ and —$SO_2R_1$ wherein $R_1$ is hydrogen, methyl or ethyl; tetrazolyl; —$NR_2R_3$, —$CH_2NR_2R_3$ and —C(=O)$NR_2R_3$ wherein $R_2$ and $R_3$ are independently hydrogen, methyl or ethyl.

8. The method as claimed in claim 1 wherein:
$Ar^2$ is 3-pyridyl, pyrimidin-4-yl, pyrazin-2-yl or pyridazin-3-yl;
$Ar^3$ is an optionally substituted divalent 1,4-phenylene or a 2,5-pyridinylene radical of formula:

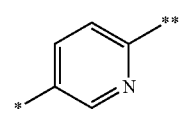

wherein the bond marked with a single asterisk is attached to $Ar^1$ and the bond marked with a double asterisk is attached to the oxygen; and
$Ar^1$ is optionally substituted phenyl.

9. The method as claimed in claim 8 wherein $Ar^1$ is phenyl, 2-fluorophenyl, 3-(2-methoxy-ethoxy)-phenyl, or 2-methoxy-5-(2-methoxy-ethoxy)-phenyl.

10. The method as claimed in claim 8 wherein $Ar^2$ is pyridazin-3-yl.

11. The method as claimed in claim 1, wherein the compound is selected from the group consisting of
3-(biphenyl-4-yloxy)-azetidine-1-carboxylic acid phenyl-amide,
3-(biphenyl-4-yloxy)-azetidine-1-carboxylic acid (3-fluoro-phenyl)-amide,
3-(biphenyl-4-yloxy)-azetidine-1-carboxylic acid (2-fluoro-phenyl)-amide,
3-(biphenyl-4-yloxy)-azetidine-1-carboxylic acid pyridin-3-ylamide,
3{-5-[3-(2-methoxy-ethoxy)-phenyl]-pyridin-2-yloxy}-azetidine-1-carboxylic acid pyrimidin-4-ylamide, 3{-5-[3-(2-methoxy-ethoxy)-phenyl]-pyridin-2-yloxy}-azetidine-1-carboxylic acid pyrazin-2-ylamide,
3{-5-[3-(2-ethoxy-ethoxy)-phenyl]-pyridin-2-yloxy}-azetidine-1-carboxylic acid pyridazin-3-ylamide,
3{-5-[3-(2-ethoxy-ethoxy)-phenyl]-pyridin-2-yloxy}-azetidine-1-carboxylic acid pyridin-3-ylamide,
3{-5-[3-(2-benzyloxy-ethoxy)-phenyl]-pyridin-2-yloxy}-azetidine-1-carboxylic acid pyridazin-3-ylamide,
3-{5-[3-(2-hydroxy-ethoxy)-phenyl]-pyridin-2-yloxy}-azetidine-1-carboxylic acid pyridazin-3-ylamide,
3-{5-[2-methoxy-5-(2-methoxy-ethoxy)-phenyl]-pyridin-2-yloxy}-azetidine-1-carboxylic acid pyridazin-3-ylamide,
3-[5-(2,5-dimethoxy-phenyl)-pyridin-2-yloxy]-azetidine-1-carboxylic acid pyridazin-3-ylamide,
3-(5-phenyl-pyridin-2-yloxy)-azetidine-1-carboxylic acid pyridazin-3-ylamide,
3-[5-(2,6-difluoro-phenyl)-pyridin-2-yloxy]-azetidine-1-carboxylic acid pyridazin-3-ylamide,
3-{5-[2-chloro-5-(2-methoxy-ethoxy)-phenyl]-pyridin-2-yloxy}-azetidine-1-carboxylic acid pyridazin-3-ylamide,
3-[5-(2-fluoro-phenyl]-pyridin-2-yloxy]-azetidine-1-carboxylic acid pyrazin-2-ylamide,
3-[5-(2-methoxy-phenyl)-pyridin-2-yloxy]-azetidine-1-carboxylic acid pyridazin-3-ylamine,
3-[5-(2-fluoro-phenyl)-pyridin-2-yloxy]-azetidine-1-carboxylic acid pyridazin-3-ylamide,
3-[5-(2-fluoro-3-methoxy-phenyl)-pyridin-2-yloxy]-azetidine-1-carboxylic acid pyridazin-3-ylamide,
3-[5-(2-fluoro-phenyl)-pyridin-2-yloxy]-azetidine-1-carboxylic acid (6-methyl-pyridazin-3-yl)-amide,
3-[5-(2-fluoro-phenyl)-pyridin-2-yloxy]-azetidine-1-carboxylic acid (6-methoxy-pyridazin-3-yl)-amide,
3-[5-(2-fluoro-phenyl)-pyridin-2-yloxy]-azetidine-1-carboxylic acid (5-methyl-[1,3,4]oxadiazol-2-yl)-amide,
3-[5-(2-fluoro-phenyl)-pyridin-2-yloxy]-azetidine-1-carboxylic acid pyridazin-4-ylamide,
3-[5-(2-fluoro-phenyl)-pyridin-2-yloxy]-azetidine-1-carboxylic acid (5-methyl-pyridazin-3-yl)-amide,
3-[5-(2-fluoro-phenyl)-pyridin-2-yloxy]-azetidine-1-carboxylic acid (4-methyl-pyridazin-3-yl)-amide,
or a pharmaceutically salt thereof.

12. The method of claim 1, wherein the disease or condition is selected from vomiting and nausea.

13. The method of claim 1, wherein the disease or condition is selected from depression, anxiety, spinal cord injury, and schizophrenia.

* * * * *